(12) United States Patent
White et al.

(10) Patent No.: US 7,141,063 B2
(45) Date of Patent: Nov. 28, 2006

(54) STENT WITH MICRO-LATCHING HINGE JOINTS

(75) Inventors: Jason White, Atlanta, GA (US); David Stern, Grayson, GA (US)

(73) Assignee: Icon Medical Corp., Cleveland, OH (US)

( * ) Notice: Subject to any disclaimer, the term of this patent is extended or adjusted under 35 U.S.C. 154(b) by 0 days.

(21) Appl. No.: 10/636,324

(22) Filed: Aug. 6, 2003

(65) Prior Publication Data

US 2004/0093077 A1 May 13, 2004

(51) Int. Cl.
*A61F 2/06* (2006.01)
*F16C 11/00* (2006.01)

(52) U.S. Cl. ........................ 623/1.15; 403/103
(58) Field of Classification Search ............... 623/1.1, 623/1.15–1.17, 1.32, 23.7; 403/104–107, 403/83, 84, 92, 93, 62, 101, 113, 119, 164, 403/173, 203, 279, 62.83
See application file for complete search history.

(56) References Cited

U.S. PATENT DOCUMENTS

| | | | |
|---|---|---|---|
| 4,776,337 A | 10/1988 | Palmaz | |
| 5,192,307 A | 3/1993 | Wall | |
| 5,266,073 A | 11/1993 | Wall | |
| 5,503,497 A | * 4/1996 | Dudley et al. | 403/103 |
| 5,582,488 A | * 12/1996 | Dudley et al. | 403/103 |
| 5,824,038 A | 10/1998 | Wall | |
| 6,974,475 B1 | 12/2005 | Wall | |

* cited by examiner

*Primary Examiner*—David J. Isabella
(74) *Attorney, Agent, or Firm*—Fay Sharpe Fagan Minnich & McKee; Brian E. Turung

(57) ABSTRACT

A stent is constructed using interconnected links having micro-mechanical latching mechanisms. The micro-mechanical latching elements allow relative rotational movement of interconnected links in one rotational direction but restrict relative rotational movement of the two links in the opposite direction. The micro-mechanical latch surface features are formed using microelectronic mechanical systems (MEMS) manufacturing methods. The male surface of the latching components contains an array of ridges or protrusions, and the receiving surface contains a matching array of recesses. The array of ridges or protrusions and the corresponding recesses have uniformly dissimilar slopes that result in a substantially greater frictional force in one direction than in the opposite direction. The separation distance between the two surfaces is such that the male latch surface is engaged with the receiving surface recesses in the low stress "locked" state, preventing motion in the undesired direction. Each male ridge or protrusion can be underlined by a void that promotes elastic deflection when sliding in the desired direction and recovery into the 'locked' state when aligned with the recesses.

48 Claims, 20 Drawing Sheets

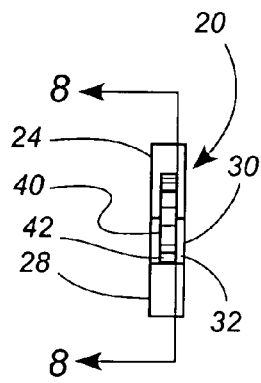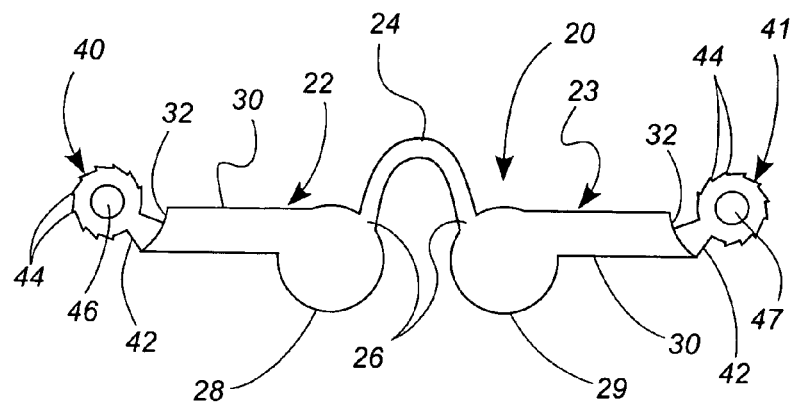
*Fig. 6*          *Fig. 5*
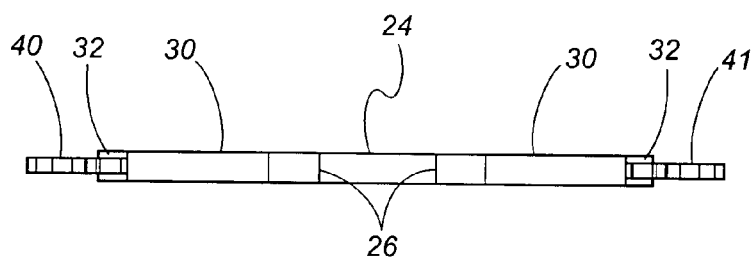
*Fig. 7*
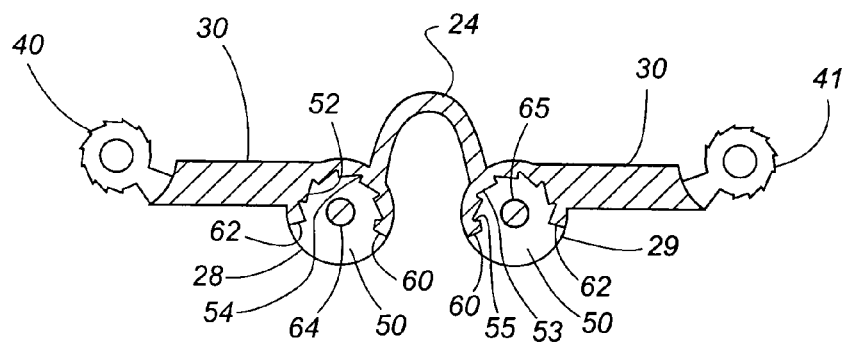
*Fig. 8*

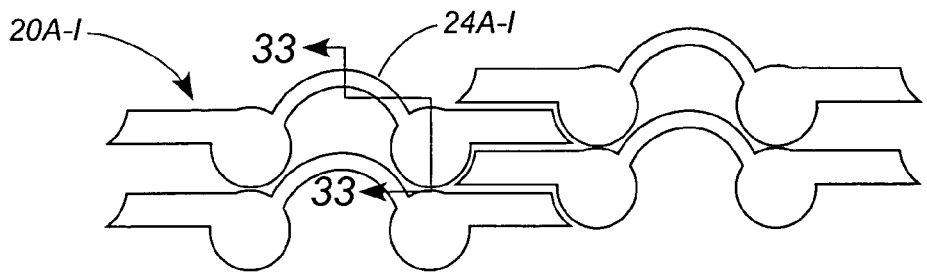
Fig. 32
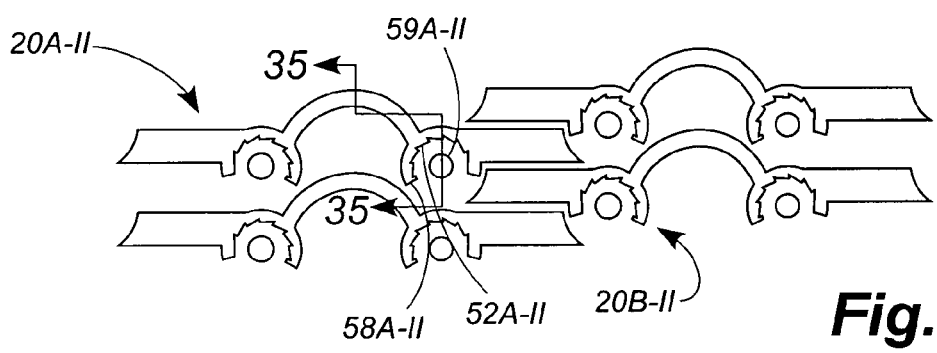
Fig. 34
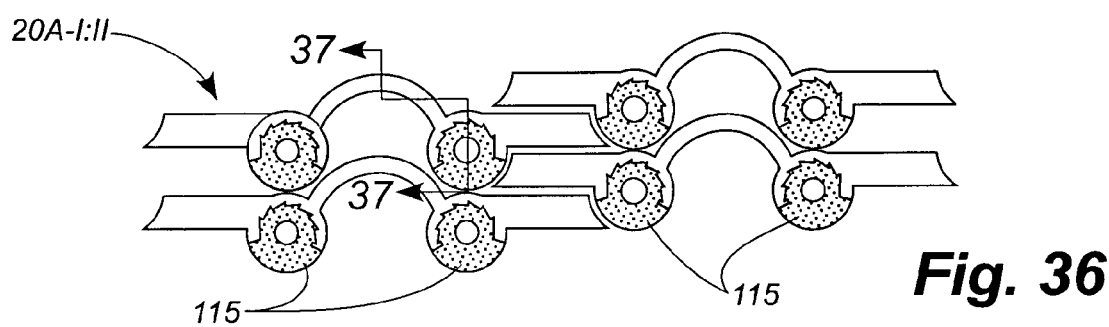
Fig. 36
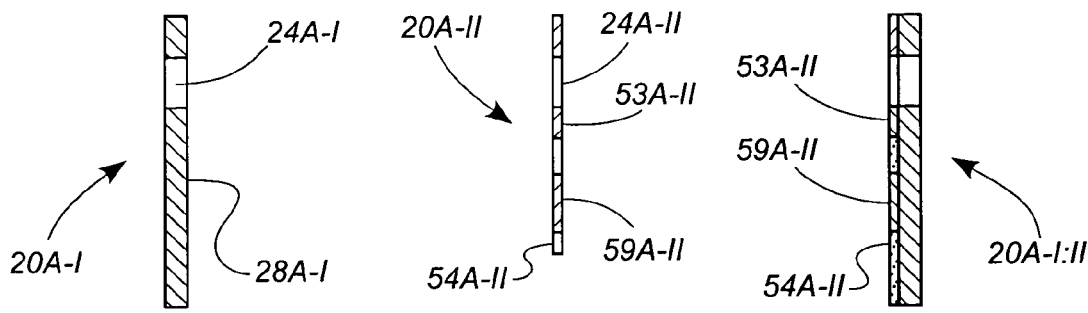
Fig. 33   Fig. 35   Fig. 37

*Fig. 49*
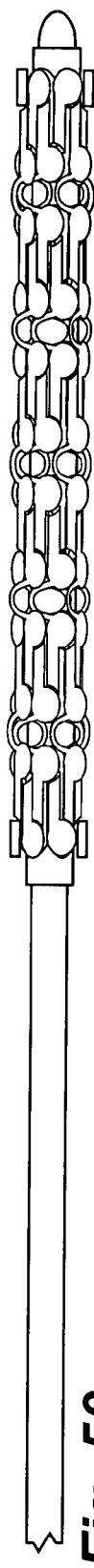
*Fig. 50*
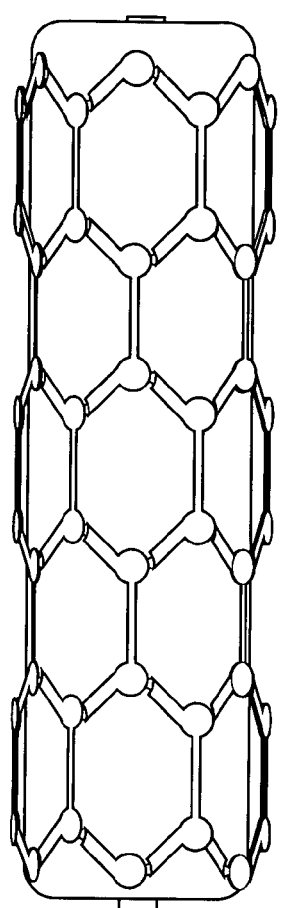
*Fig. 51*
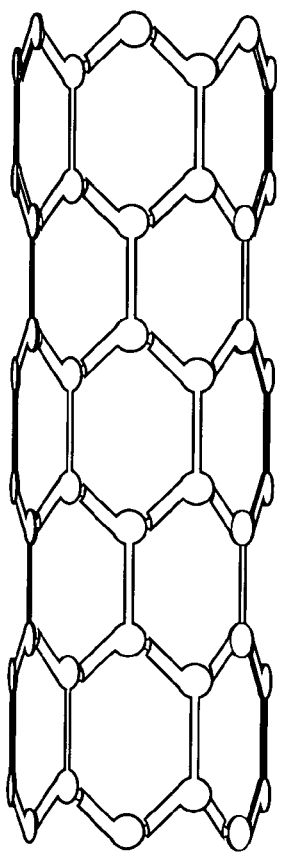
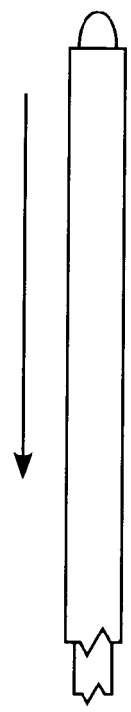
*Fig. 52*

STENT WITH MICRO-LATCHING HINGE JOINTS

TECHNICAL FIELD

The present invention relates generally to medical devices, more particularly stents. More specifically, the present invention relates to an expandable stent that comprises micro-latching hinge joints that permit the stent to expand and thereafter maintain the stent in its expanded configuration.

BACKGROUND OF THE INVENTION

Stents are generally tubular devices used to prop open a segment of blood vessel or other anatomical lumen. They are useful in the treatment of atherosclerotic stenosis in blood vessels, maintaining blood perfusion to downstream tissue after opening of a flow restriction.

Various different types of stent designs have been developed for treating diseases of the blood vessels and other tubular structures inside the body. The currently available stents can be classified into two broad categories: balloon-expandable and self-expanding.

A balloon-expandable stent, as described in U.S. Pat. No. 4,776,337, is crimped down onto a folded balloon on the end of a balloon dilatation catheter. When the stent has been properly positioned within the vessel lumen, the balloon is inflated to an appropriate pressure, opening the stent to the desired diameter. The balloon is deflated and the stent remains in its expanded state, due to the plastic deformation that was imparted to its structural elements during expansion.

A balloon-expandable stent has many attractive attributes. Its diameter and outward force to the vessel wall can be adjusted by the inflation pressure of the balloon. After deployment, the stent is a semi-rigid structure that can conform to some extent longitudinally, but maintains a rigid scaffolding that prevents vessel collapse in the radial direction. However one disadvantage to balloon-expandable stents is that there is typically some component of elastic recoil after expansion as long as the mechanism for change between the crimped state to the expanded state is through deformation of the structural elements. This usually means that there is a reduction in diameter after the balloon is deflated. The degree of reduction in diameter is related to the material selection, structural design, and degree of inward force from the vessel wall. These factors vary from stent to stent and situation to situation, presenting a challenge for the practitioner to achieve the desired outcome in repeatable manner.

Traditional balloon-expandable stents change configuration from the crimped to the expanded state through the opening of the angle between radial support members during balloon expansion. In the process, cold work is imparted at the intersections of the structural radial expansion units. Once the expansion is complete, the crystalline structure of the bulk material at the intersections remains in the expanded configuration, minus the minimal elastic recovery.

Achieving this described effect is entirely dependent on the bulk properties of the stent material. For this reason, the material selection is limited to a material that plastically deforms at relatively low strain levels, with a minimal degree of elastic recovery. Materials that fit this description are typically metals. These material requirements are directly in conflict with other secondary desirable attributes of a stent, such as flexibility, biodegradability, and the ability to serve as a platform for drug delivery.

For these reasons, metal is a sub-optimal material selection for these secondary performance categories. However, expandability and radial strength are both primary requirements of a stent, and so metals have been the most viable material option in present day balloon-expandable stents.

Balloon-expandable and self-expanding stents are known that employ ratcheting or latching means for expansion and retaining the expanded configuration. One purported benefit of stent designs that contain latching elements is the capability for more precise lumen sizing. In the balloon-expandable latching stent designs, a latch allows radial expansion but limits post deployment reduction in diameter. In the self-expanding case, a latch can be employed to prevent over-expansion. The latch also provides an upper limit to the chronic outward force on the vessel.

Perhaps the most important benefit of a latching stent design is that the expansion mechanism is not entirely dependent on the bulk deformation of the stent material. This benefit makes possible the use of non-metallic materials in the construction of a latching stent and potentially enables the use of a material that would be better suited to optimize the more secondary performance attributes, such as flexibility, biodegradability, and drug delivery.

However, an important distinction between this prior art and the present invention is that the previously described latching mechanisms are on the same order of scale as the other stent design elements. Furthermore, no specialized micro-fabrication method is specified in order to create the latching elements. There are several undesirable characteristics that result from these important differences.

In practice, one of the general drawbacks to stent-latching mechanisms has been that the latching mechanisms themselves add an additional element that provides additional bulk to the device. For this reason the inclusion of a conventional latch presents reduced flexibility and a larger undeployed profile, i.e., diameter. These characteristics are important because they relate to the ability for the stent to be able to reach a desired delivery site. The flexibility of the stent is a major factor in how well the stent is able to navigate turns in the vessel, and the diameter of the stent determines the minimum cross-sectional restrictions in the vessel that can be traversed by the stent prior to reaching the delivery site. Additionally a larger profile stent requires that larger accessory devices be used to introduce the device. This means that the puncture site to the vessel for introducing the stent must be larger as well, leading to longer post-procedure patient recovery times.

Another drawback to standard stent-latching mechanisms has been that the sizing increment is not continuous. Thus if a desired stent diameter falls between two latch states, the stent must be adjusted to a size which is either too large or too small for the intended application. The sizing increment that is available to the user is typically a function of the size and spacing between latching mechanisms. So the expanded stent diameter increment of adjustability is restricted, when compared to non-latching, balloon-expandable stents. This effect becomes more significant as the size of the target vessel becomes smaller, and so the use of the previously proposed ratcheting stents are practical only with larger, non-coronary vessels.

Thus there is a need for a stent with a latching mechanism which does not appreciably add to the size of the stent or reduce the interior diameter of the stent.

There is a further need for a stent with a latching mechanism which provides virtually continuous adjustment, that is, the increment between adjacent latch states is minimal.

SUMMARY OF THE INVENTION

The present invention relates to a radially expandable stent for use in an artery or any other body lumen. It is comprised of radially expandable structural members with micro latches incorporated in their joints. The micro latches allow growth of the angle between the structural members in the direction that results in radial expansion of the structure, but restricts change of the angle between the structural members in the reverse direction.

Objects, features, and advantages of the present invention will become apparent upon reading the following specification, when taken in conjunction with the drawings and the appended claims.

BRIEF DESCRIPTION OF THE DRAWINGS

FIG. 5 is a side view of a link of the expandable stent of FIG. 1.

FIG. 6 is an end view of the link of FIG. 5.

FIG. 7 is a top view of the link of FIG. 5.

FIG. 8 is a side cutaway view taken along line 8—8 of FIG. 6.

FIGS. 32–48 depict a manufacturing process by which a panel of links of the type shown in FIG. 5 are manufactured by building up a series of layers, where:

FIG. 32 shows a first layer;

FIG. 33 is a cross-sectional view taken along line 33—33 of FIG. 32;

FIG. 34 shows a second layer;

FIG. 35 is a cross-sectional view taken along line 35—35 of FIG. 34;

FIG. 36 shows the second layer of FIG. 34 imposed onto the first layer of FIG. 32;

FIG. 37 is a cross-sectional view taken along line 37—37 of FIG. 36;

FIG. 38 depicts a third layer;

FIG. 39 is a cross-sectional view taken along line 39—39 of FIG. 38;

FIG. 40 shows the third layer of FIG. 38 imposed onto the first and second layers of FIG. 36;

FIG. 41 is a cross-sectional view taken along line 41—41 of FIG. 40;

FIG. 42 illustrates a fourth layer;

FIG. 43 shows the fourth layer of FIG. 42 imposed onto the first three layers of FIG. 40;

FIG. 44 is a cross-sectional view taken along line 44—44 of FIG. 43;

FIG. 45 depicts the fifth layer of the manufacturing process;

FIG. 46 shows the fifth layer of FIG. 45 imposed onto the first three layers of FIG. 43;

FIG. 47 is a cross-sectional view taken along line 47—47 of FIG. 46; and

FIG. 48 is a cross-sectional view of the finished product.

FIG. 49 is a side view of a balloon catheter up the type used to install the catheter are FIG. 1.

FIG. 50 is a side view of the balloon catheter of FIG. 49 with the stent of FIG. 1 in its unexpanded configuration mounted to the catheter.

FIG. 51 is a side view showing the balloon of the catheter of FIG. 49 inflated to expand the stent.

FIG. 52 shows the balloon catheter deflated and withdrawn, between the expanded stent of FIG. 52 in place.

FIG. 53 is a side view of the link of the alternate embodiment; that will have a FIG. 54 is a side view showing two link segments of an adjoining pair of links in an unexpanded configuration;

DETAILED DESCRIPTION OF THE DISCLOSED EMBODIMENT

Figure 1:
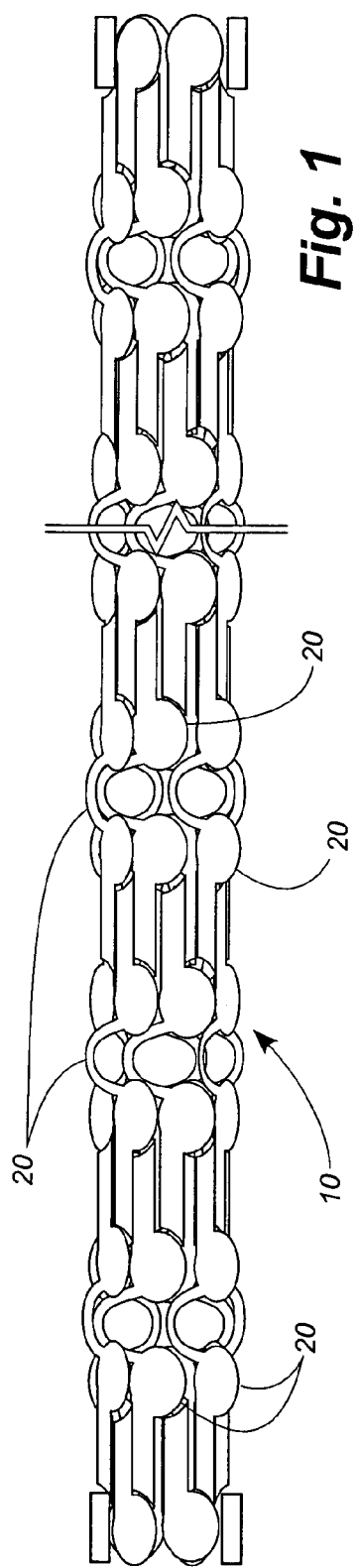
FIG. 1 is a side view of a stent with micro latching features, showing the stent in a contracted configuration according to a disclosed embodiment of the present invention.
Figure 3:
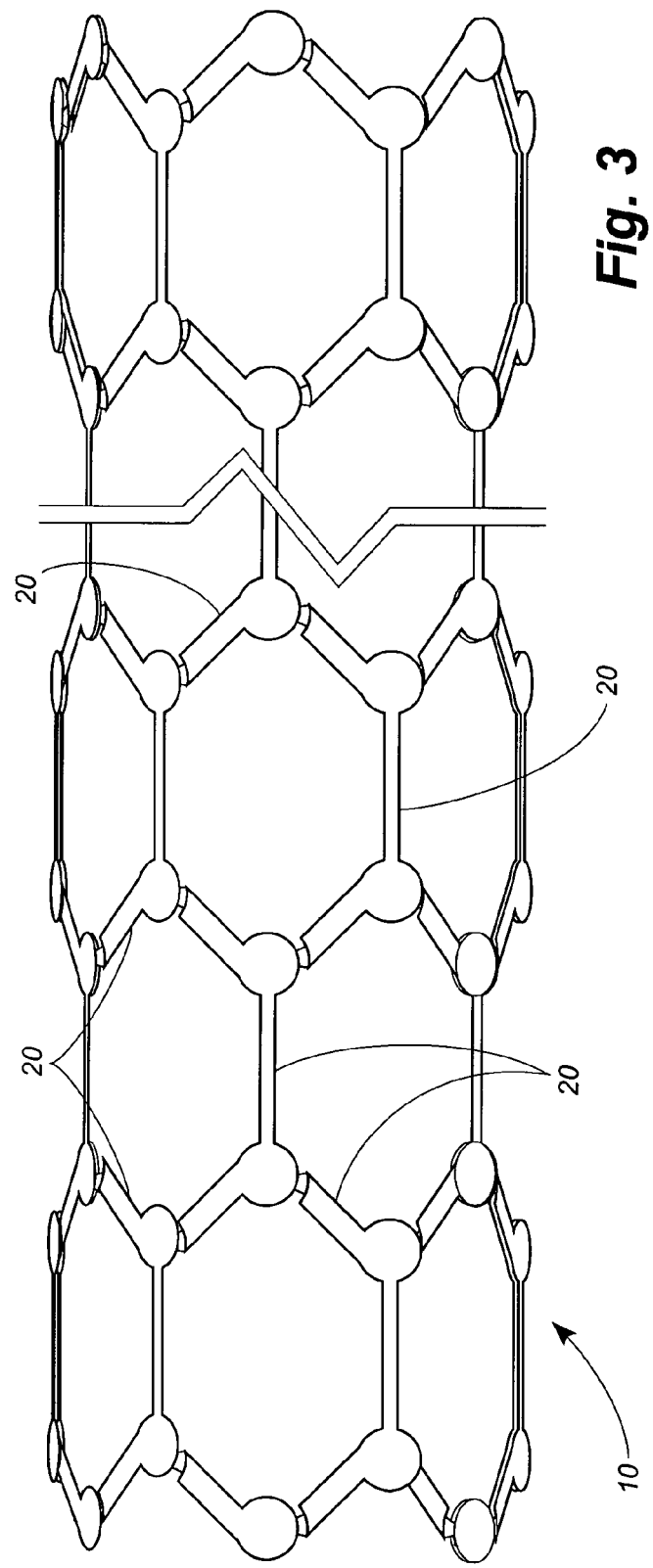
FIG. 3 is a side view of the stent of FIG. 1 in an expanded configuration.
Figure 2:
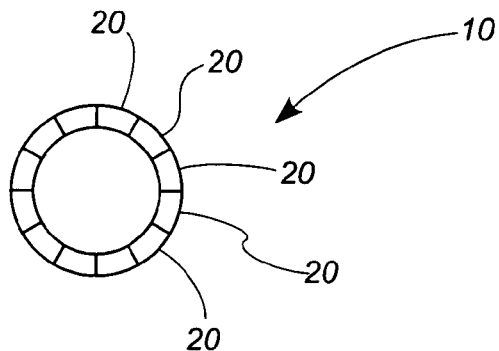
FIG. 2 is an end view up the stent of FIG. 1.
Figure 4:
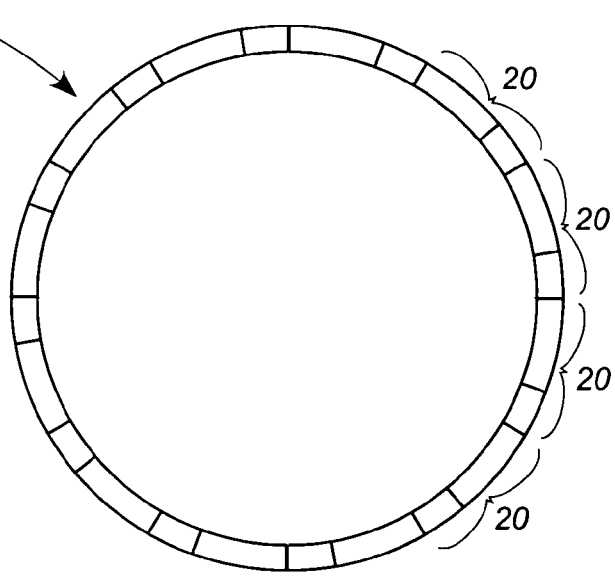
FIG. 4 is an end view of the stent of FIG. 3.

Referring now to the drawings, in which like numerals indicate like elements throughout the several views, FIGS. 1–4 show a stent 10 according to a disclosed embodiment of the present invention. The stent 10 is comprised of a plurality of links 20. FIGS. 1 and 2 show the stent 10 in its unexpanded configuration, in which the stent has a length of approximately 35 mm and a diameter of approximately 2 mm. FIGS. 3 and 4 show the stent 10 in an expanded configuration, in which the stent has a length of approximately 35 mm and a diameter of approximately 7 mm. Thus the diameter of the stent 10 expands to approximately three-and-a-half times its unexpanded diameter, while the length of the stent remains virtually unchanged.

It will be understood that the dimensions of the stent 10 are disclosed only by way of example, and that the stent can be manufactured of any size suitable for the body lumen into which the stent is to be installed. As will be apparent, the dimensions of the stent 10 can be modified by increasing or decreasing the number of links 20, by increasing or decreasing the size of the links 20, or any combination of the two.

Figure 61:
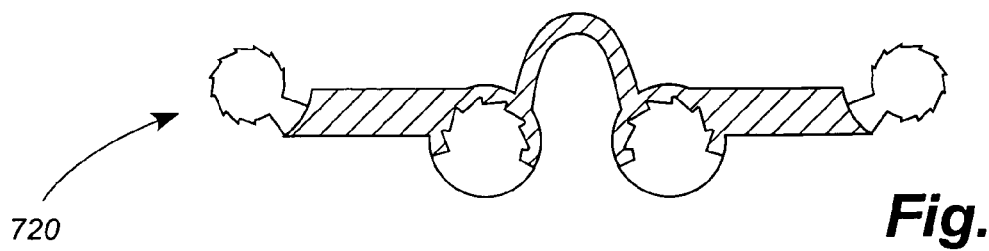
FIG. 61 is another embodiment of a link.

A link 20 is shown in more detail in FIGS. 5–61. The link 20 is a unitary structure comprising left and right link segments 22, 23 joined by a connector 24. The ends of the connector 24 are joined to the link segments 22, 23 at junctions 26. Each link segment 22, 23 includes a disk-shaped head portion 28, 29 respectively, also referred to herein as a "containment joint." A radial support member 30 extending substantially tangentially outward from each of the head portions 28, 29. The radial support members 30 of the respective link segments 22, 23 extend in opposite directions from one another. Each radial support member 30 includes a face 32 at its free end.

Unless otherwise stated, terms used herein such as "top," "bottom," "upper," "lower," "left," "right," "front," "back," "proximal," "distal," and the like are used only for convenience of description and are not intended to limit the invention to any particular orientation.

A first toothed wheel 40 is located at the free end of the left link segment 22, and a second toothed wheel 41 is located at the free end of the right link segment 23. The toothed wheels 40, 41 are connected to the end face 32 of the corresponding radial support member 30 by a neck portion 42. Each of the wheels 40, 41 has a plurality of gear teeth 44 formed on a major portion of its periphery. The toothed wheels 40, 41 are mirror images of one another, that is, the gear teeth 44 on the first toothed wheel 40 are oriented in the opposite direction from the gear teeth 44 on the second toothed wheel 41. A circular bore 46 is formed in the center of the first toothed wheel 40, and a circular bore 47 is formed in the center of the second toothed wheel 41.

Figure 9:
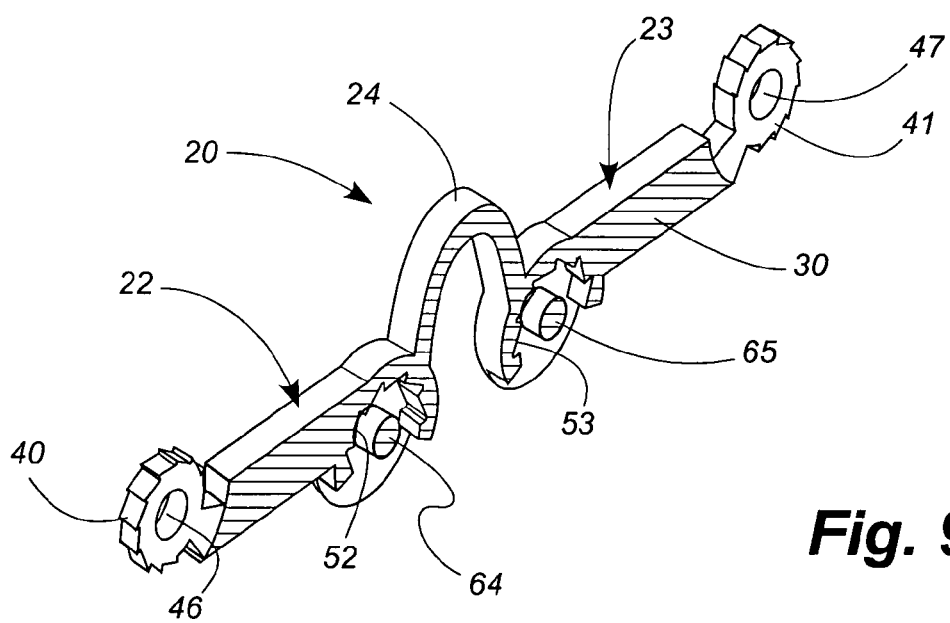
FIG. 9 is a perspective view of the cutaway link of FIG. 8.
Figure 10:
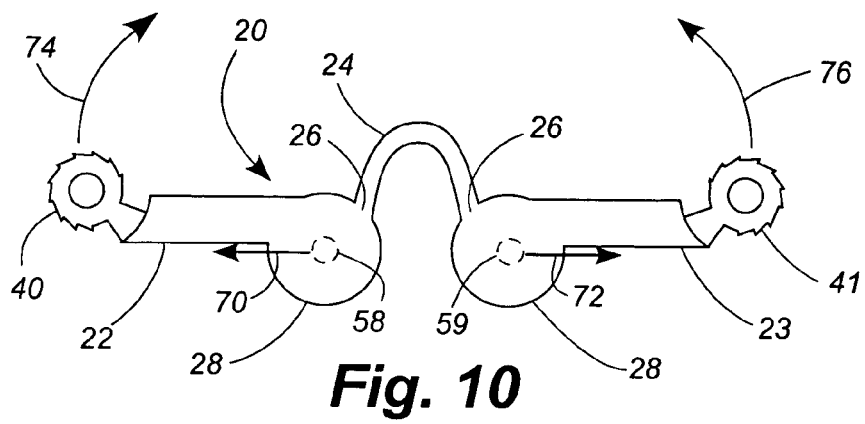
FIG. 10 is a side view of the link of FIG. 5 illustrating how the link is bent from a contracted configuration into an expanded configuration.

FIGS. 8 and 9 are cut away to reveal the interior detail of the disk-shaped head portions 28, 29 of the link 20. A cavity 50 is formed in the lower section of each head portion 28, 29. The bottom of the cavity 50 is open. A wall 52 defines the upper boundary of the cavity 50 in the left link segment 22, and a wall 53 defines the upper boundary of the cavity 50 in the right link segment 23. The walls 52, 53 are formed with tooth-shaped recesses 54, 55 respectively, corresponding generally to the outer periphery of the toothed wheels 40, 41. The walls 52, 53 are mirror images of one another, that is, the tooth-shaped recesses 54 of the first wall 52 are oriented in the opposite direction from the tooth-shaped recesses 55 of the second wall 53. The ends 60, 62 of the walls 52, 53 serve as stops, as will be explained below. A first cylindrical spindle 64 is formed in the center of the head portion 28 of the left link segment 22, and a second cylindrical spindle 65 is formed in the center of the head portion 28 of the right link segment 22 FIG. 10 illustrates the manner in which a link 20 can be deformed from a first configuration to a second configuration. Opposite and outward forces are exerted on the spindles 64, 65 in the directions indicated by the arrows 70, 72. The forces 70, 72 tend to straighten the connector 24 and displace the head portions 28 of the respective link segments 22, 23 away from one another. The downward displacement of the connector 24 causes the junctions 26 between the connector 24 and the respective link segments 22, 23 to be rotated downward. This downward displacement of the junctions 26 causes the left link segment 22 to rotate in a clockwise direction, as indicated by the arrow 74, and causes the right link segment 23 to rotate in a counterclockwise direction, as indicated by the arrow 76.

Figure 11:
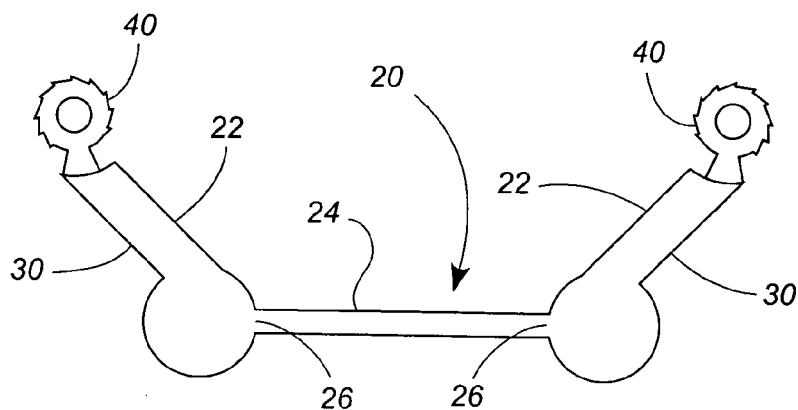
FIG. 11 is a side view of the link of FIG. 5 in an expanded configuration.

In response to these actions, the link 20 assumes the configuration shown in FIG. 11. The connector 24 is now substantially horizontal. The junctions 26 between the ends of the connector 24 and the respective link segments 22, 23 have been displaced downward from the one o'clock and eleven o'clock positions shown in FIG. 9 to the three o'clock and nine o'clock positions shown in FIG. 10. The radial support members 30 of both link segments 22, 23 are angled upward at approximately a forty-five degree angle.

Figure 12:
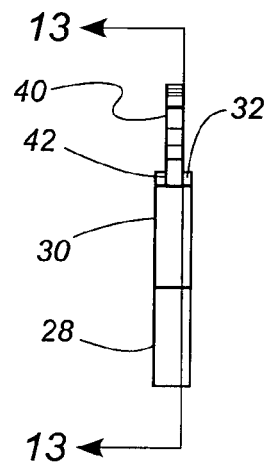
FIG. 12 is an end view of the expanded link of FIG. 11.
Figure 13:
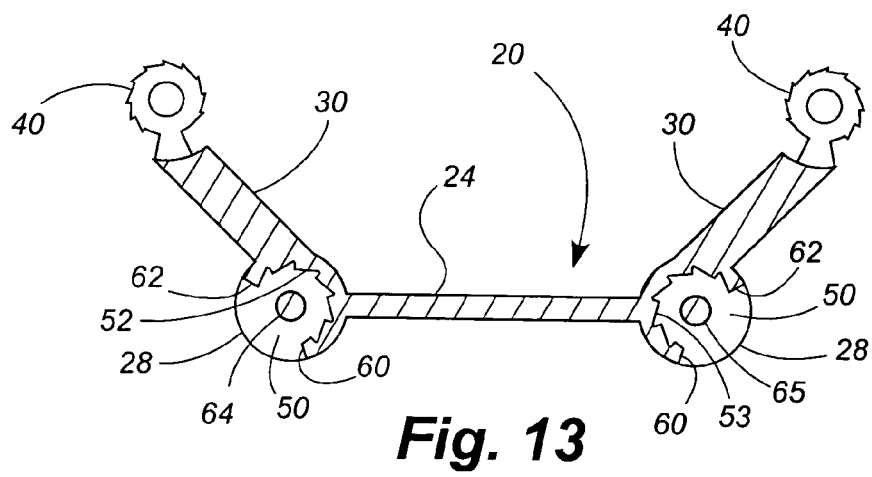
FIG. 13 is a side cutaway view taken along line 13—13 of FIG. 12.

For purposes of discussion, the configuration of the link 20 shown in FIGS. 5–10 will hereafter be referred to as its "normal," "unexpanded," or "contracted" configuration, and the configuration shown in FIGS. 11–13 will be referred to as the "expanded" configuration of the link 20.

Of note, when the normal configuration of FIG. 10 is compared to be expanded configuration of FIG. 11, the width of the link 20 is substantially the same. This result is achieved by selection of the length and curvature of the connector 24. For example, the change in the width of the radial support member 30, as measured in a horizontal direction, decreases from a width W in its normal configuration to a width of 0.71 W (the tangent of 45°) in its expanded state. The curvature and length of the connector 24 must therefore be selected such that, when the connector is straightened, the length of the connector as measured a horizontal direction increases by a distance of 0.58 W (2×(W–0.71)).

FIGS. 11–13 are various views illustrating the link 20 in its expanded configuration and depict essentially the same features as FIGS. 5–9 previously described.

Figure 14:
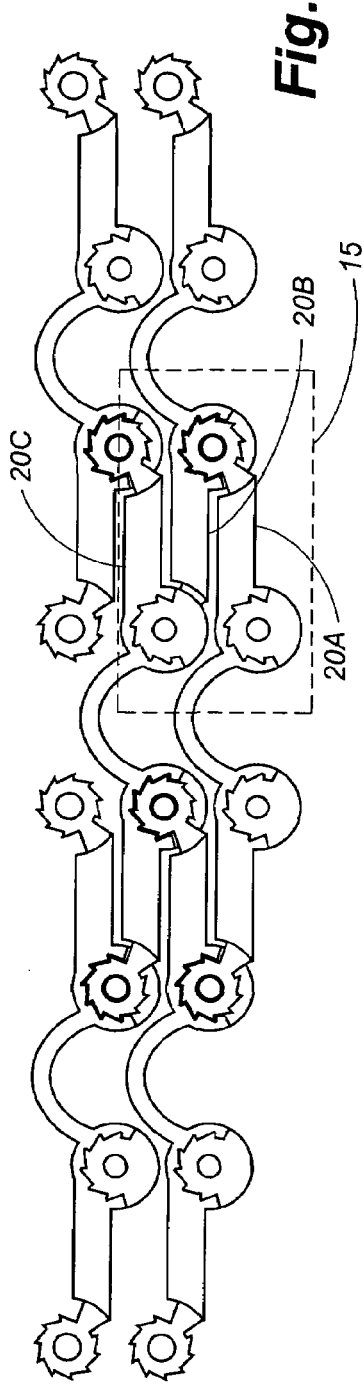
FIG. 14 is a side view of a series of interconnected links of the type and configuration illustrated in FIG. 5.

FIG. 14 shows a series of interconnected links 20, with each link shown in its normal or contracted configuration. As will be seen, the links 20 can be interconnected to form a series of rows and columns of indeterminate length. However, for ease of illustration, FIG. 14 shows only six links, arranged in three columns.

Since all of the links 20 interconnect with adjacent links in the same manner, the structure by which the links 20 interconnect will be explained in conjunction with FIGS. 14–17 with reference to three links, designated 20A, 20B, and 20C. The elements of each link will be given the same reference numerals as used hereinabove, followed by a letter "A," "B," or "C" to indicate whether the element is part of link 20A, 20B, or 20C. For example, the link and its connector have previously been assigned the reference numerals "20" and "24," so link "A" will be designated "20A" and will have a connector "24A," etc.

The links 20 interconnect with adjacent links by way of a toothed wheel 40 or 41 engaging a corresponding spindle 58 or 59 of an adjacent link. To understand the manner in which the links 20 interconnect, it should be noted that the pattern of gear teeth 44 on the toothed wheel 40 on the left link segment 22 of a given link 20 is oriented in the opposite direction from the tooth-shaped recesses in the wall 52 of the same link segment 22 but is oriented in the same direction as the tooth-shaped recesses in the wall 53 of the opposite link segment 23. Similarly, the pattern of gear teeth 44 on the toothed wheel 41 on the right link segment 23 of a given link 20 is oriented in the opposite direction from the tooth-shaped recesses in the wall 53 of the same link segment 23 but is oriented in the same direction as the tooth-shaped recesses in the wall 52 of the opposite link segment 22. Thus the toothed wheel 40 on the left link segment 22 of a given link 20 can engage only a spindle 59 on the right link segment 22 of an adjacent link, and the toothed wheel 41 on the right link segment 23 of a given link 20 can engage only a spindle 58 on the left link segment 22 of an adjacent link 20.

Referring further to FIG. 14, a section of a panel 80 of interconnected links 20 is illustrated, with the links 20 in their normal or contracted state. While the section of the panel 80 illustrated in FIG. 14 has links arranged in four rows and three columns, it will be understood that the number of rows and columns can be extended or reduced as needed to construct a panel 80 of desired dimensions. With particular reference to the links in the rectangle 15, a first link 20A is connected to a second link 20B, which in turn is connected to a third link 20C.

Figure 15:
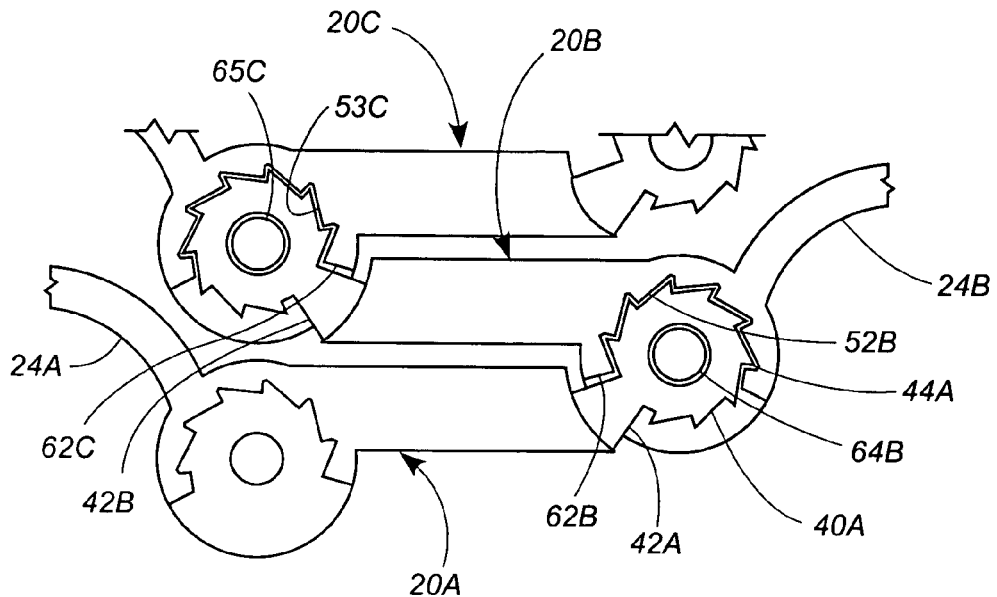
FIG. 15 is an enlarged view of the section of FIG. 14 identified by the rectangle 15.

FIG. 15 is a cutaway view of links 20A, 20B, and 20C shown by the rectangle 15 in FIG. 14. The wheel 41A of the right link segment 23A of the first link 20A is engaged in the cavity 50B of the left link segment 22B of the second link 20B. The spindle 58B of the link segment 22B engages the hole 47A of the wheel 41A. The gear teeth 44A on the periphery of the wheel 41A engage the corresponding tooth-shaped recesses in the wall 53B. The wall 54B acts as a stop, interfering with the neck 42A to prevent the wheel 41A from rotating any further in a clockwise direction with respect to the link 20B. As can be seen from FIG. 15, the orientation of the gear teeth 44A on the periphery of the wheel 41A and the corresponding tooth-shaped recesses in the wall 52B permit the wheel 41A to rotate in a counterclockwise direction with respect to the link 20B but prevent rotation of the wheel 41A in a clockwise direction. Thus the walls 52, 53 serve as female containment joints to permit rotation of the toothed wheels 40, 41 in only one direction.

Similarly, the wheel 40B of the left link segment 22B of the second link 20B is engaged in the cavity 50C of the right link segment 23C of the third link 20C. The spindle 59C of the link segment 23C engages the hole 46B of the wheel 40B. The gear teeth 44B on the periphery of the wheel 40B engage the corresponding tooth-shaped recesses in the wall 52C. The wall 54C acts as a stop, interfering with the neck 42B to prevent the wheel 40B from rotating any further in a counterclockwise direction with respect to the third link 20C. As can be seen from FIG. 15, the orientation of the gear teeth 44B on the periphery of the wheel 40B and the corresponding tooth-shaped recesses in the wall 53C permit the wheel 40B to rotate in a clockwise direction with respect to the link 20C but prevent rotation of the wheel 40B in a counterclockwise direction.

Figure 16:
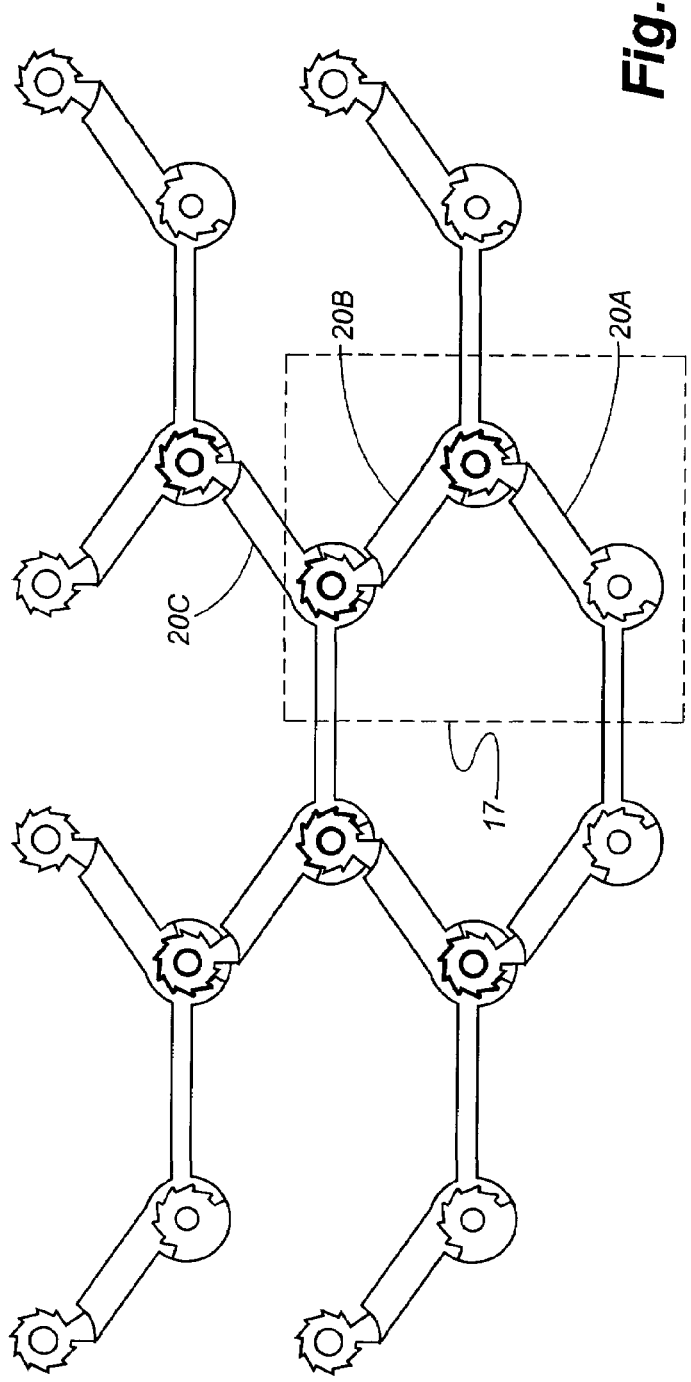
FIG. 16 is a side view of the series of interconnected lengths of FIG. 14 showing the links in the expanded configuration of FIG. 11.

Referring now to FIG. 16, the panel 80 is shown in its expanded state. The connectors 24 of the various links 20 are straightened to a substantially horizontal position, and the radial support members 30 are angled upward at approximately forty-five degree angles. With particular reference to the links in the rectangle 15, the first link 20A is again connected to the second link 20B, which in turn is connected to the third link 20C.

Figure 17:
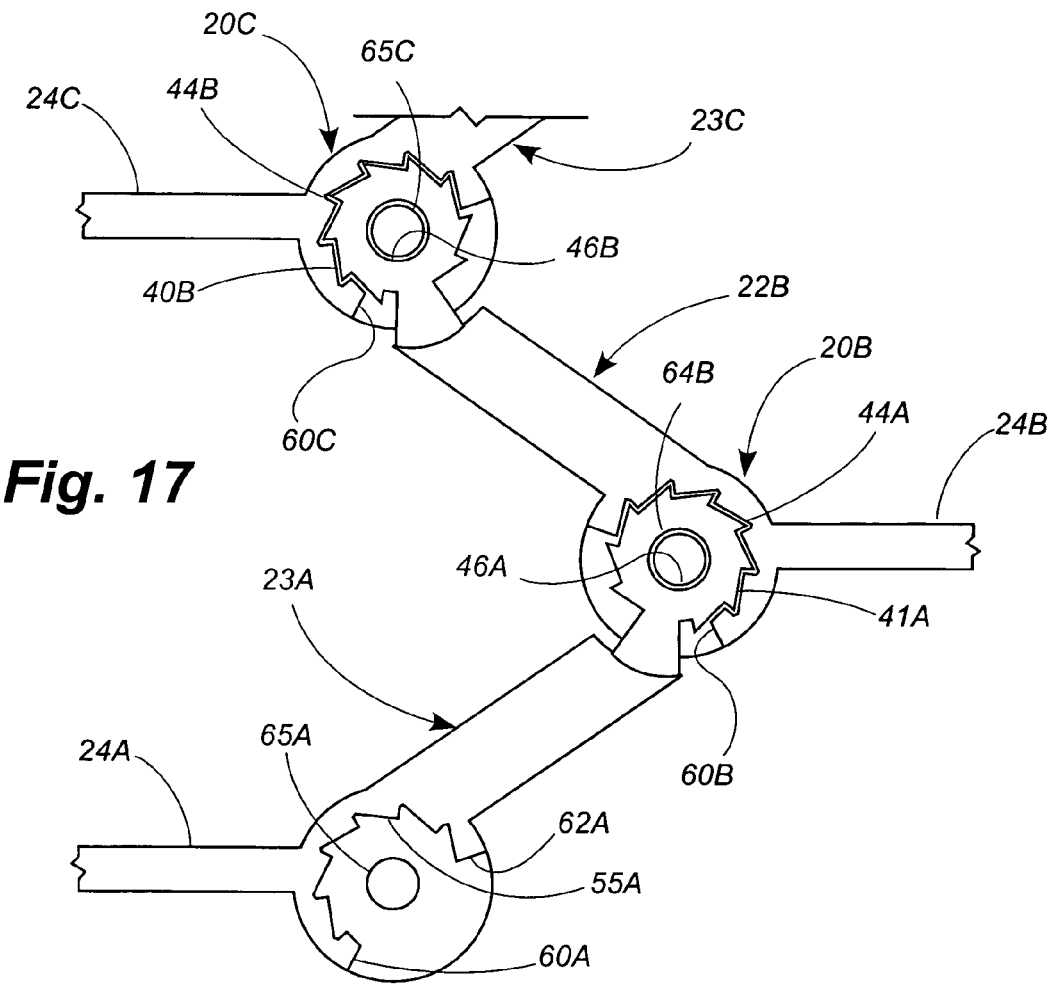
FIG. 17 is an enlarged view of the section of FIG. 16 identified by the rectangle 17.

FIG. 17 is a cutaway view of the links 20A, 20B, and 20C shown in the rectangle 17 of FIG. 16. link segment 23A of the first link 20A has rotated in a counterclockwise direction by approximately forty-five degrees. The juncture 26A where the connector 24A joins the link segment 23A has rotated from approximately an eleven o'clock position to a nine o'clock position, and the connector 24A has substantially straightened. Similarly, the link segment 22B of the second link 20B has rotated in a clockwise direction by approximately forty-five degrees. The juncture 26B where the connector 24B joins the link segment 22B has been displaced from approximately the one o'clock position to the three o'clock position, and the connector 24B has substantially straightened.

In the process of the link segments 23A, 22B rotating by approximately forty-five degrees in opposite directions, the wheel 41A of the first link 20A has rotated approximately ninety degrees within the cavity 50B of the link segment 22B. The wall 56B acts as a stop to prevent over-rotation of the wheel 41A in a counterclockwise direction with respect to the link segment 20B.

Similarly, the link segment 23C of the third link 20C has rotated by approximately forty-five degrees in a counterclockwise direction. The connector 24C of the third link 20C has rotated to a substantially horizontal orientation and has straightened. The wheel 40B at the end of the link segment 22B of the second link 20B has rotated approximately ninety degrees within the cavity 50C of the third link 20C. The wall 56C acts as a stop to prevent over-rotation of the wheel 40B in a clockwise direction.

Figure 18:
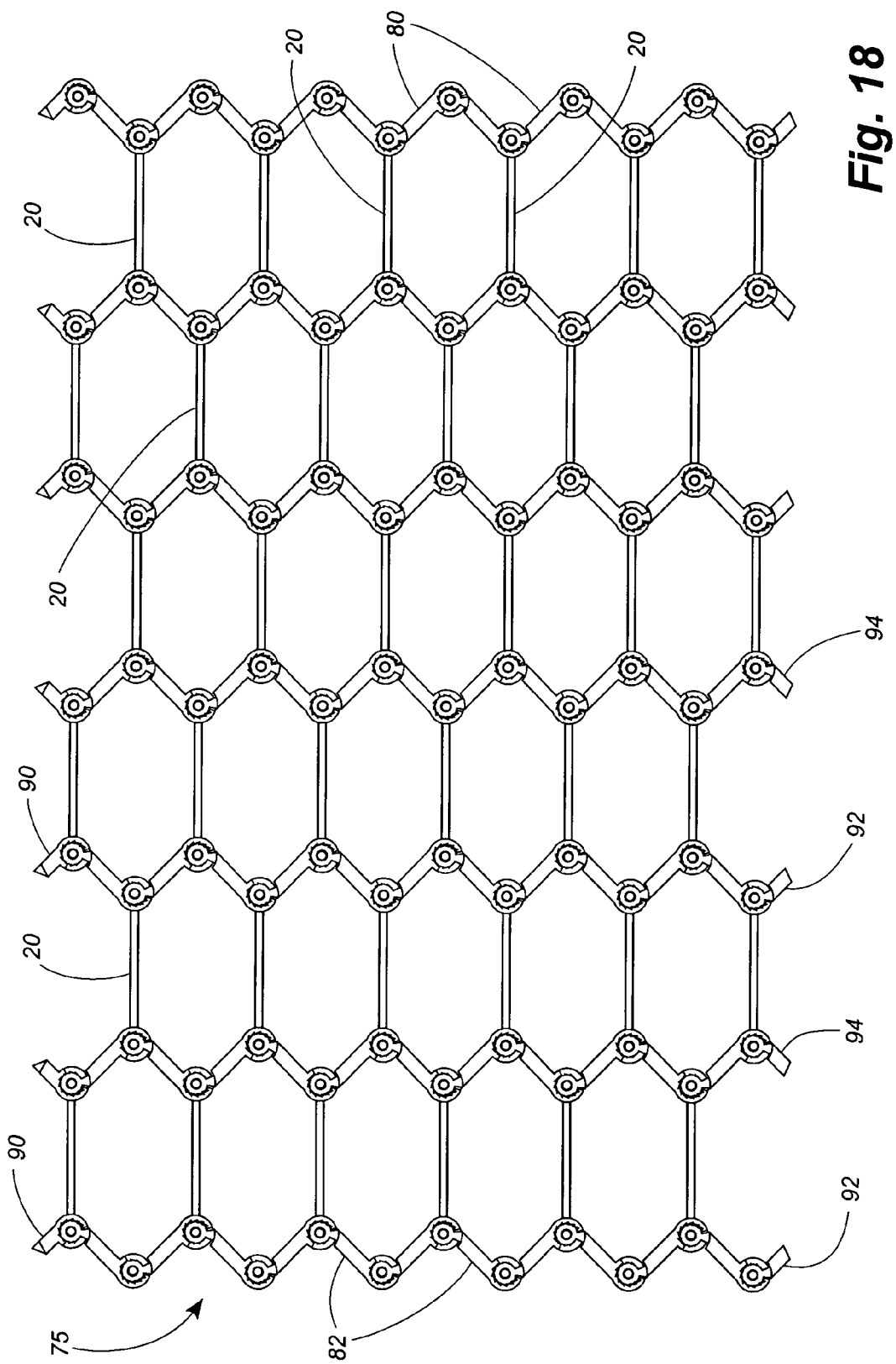
FIG. 18 is a side view of a panel of links ready for fabrication into a stent of the type shown in FIGS. 1–4.

FIG. 18 illustrates the panel 75 of interlocking links 20. In addition to the links 20, the panel 75 includes termination links 80, 82 for terminating the lateral edge is of the panel 75, and coupler links 90, 92, and 94 for joining the top and bottom edges of the panel 75 when it has been rolled into a cylinder. The termination links 80, 82 and the coupler links 90, 92, and 94 will now be described in more detail.

Figure 19:
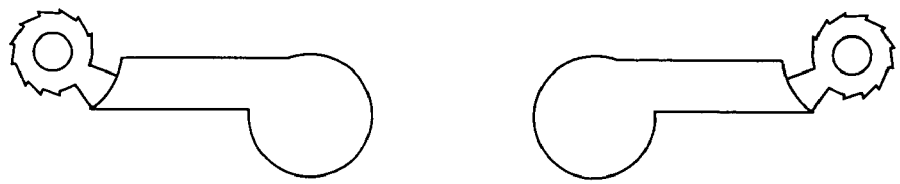
FIG. 19 is a side view of two termination links used to terminate the lateral edges of the panel of FIG. 18.
Figure 20:
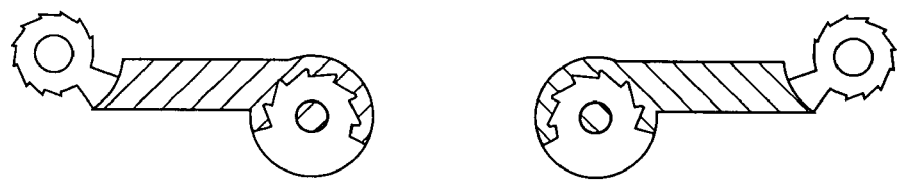
FIG. 20 is a cutaway view of the termination links of FIG. 19.
Figure 21:
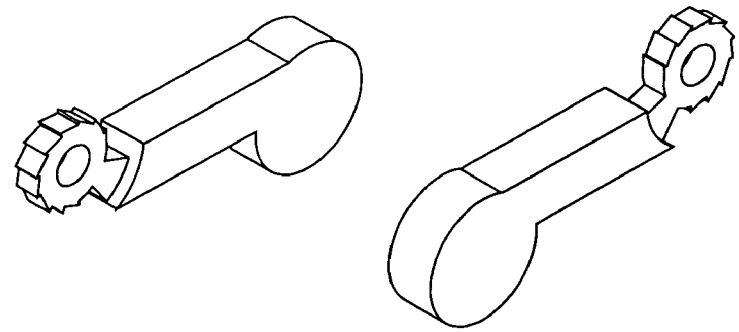
FIG. 21 is a perspective view of the termination links of FIG. 19.
Figure 22:
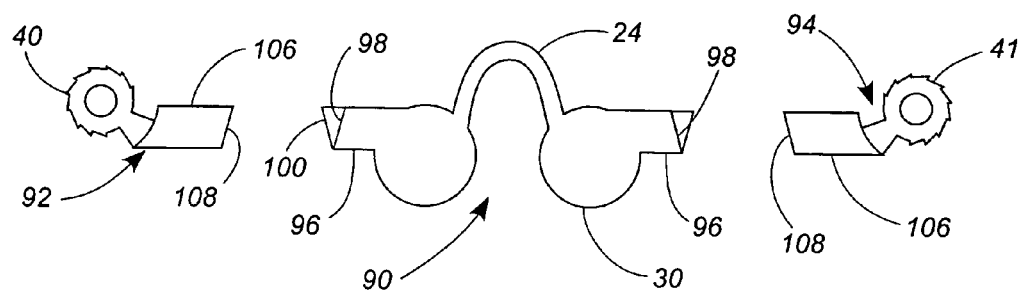
FIG. 22 is a side view of a set of connector links of a type used to join the opposite longitudinal edges of a panel of interconnected links to form a cylinder, with the segments of the connector links separated.
Figure 23:
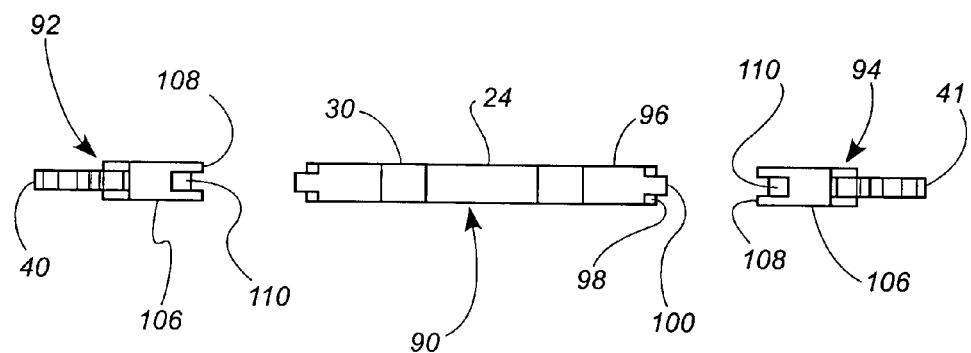
FIG. 23 is a top view of the separated connector links of FIG. 22.
Figure 24:
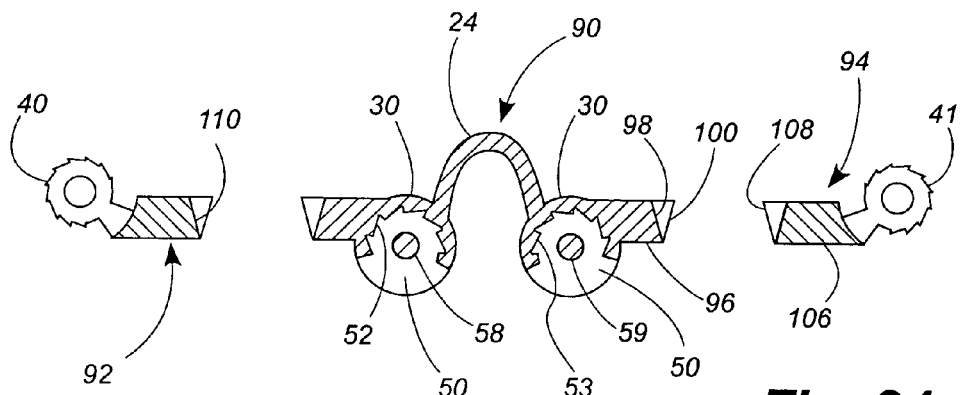
FIG. 24 is a cutaway view of FIG. 23.
Figure 25:
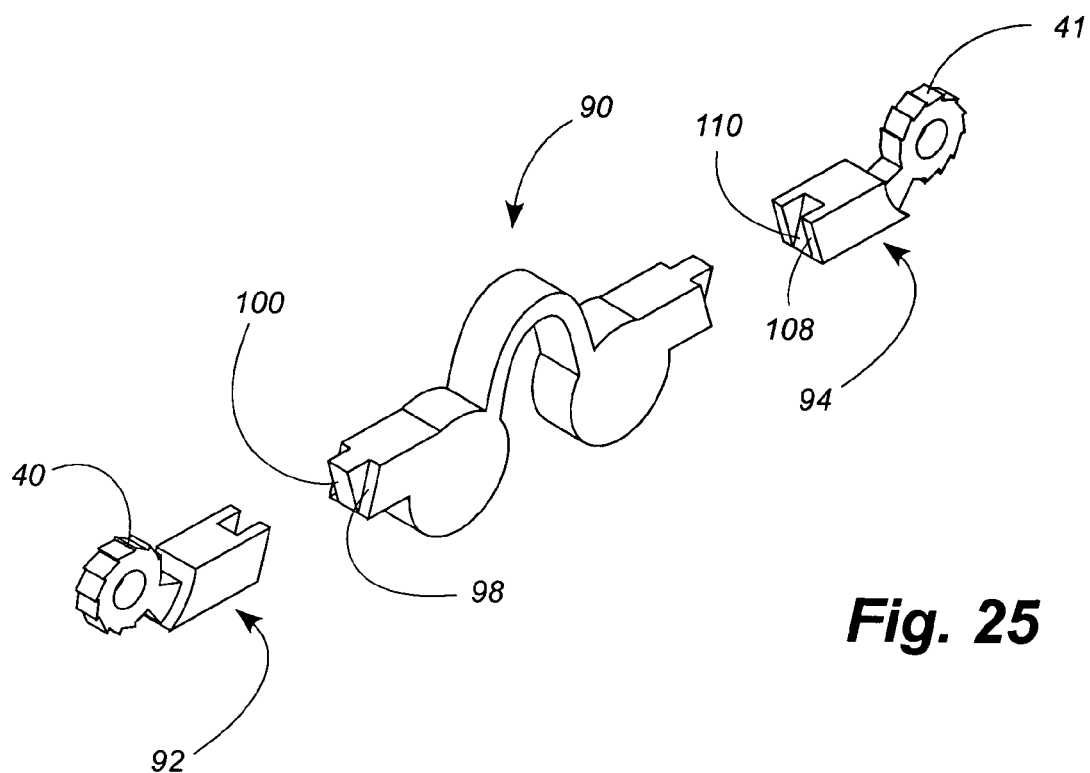
FIG. 25 is a perspective view of the separated connector links of FIG. 22.
Figure 29:
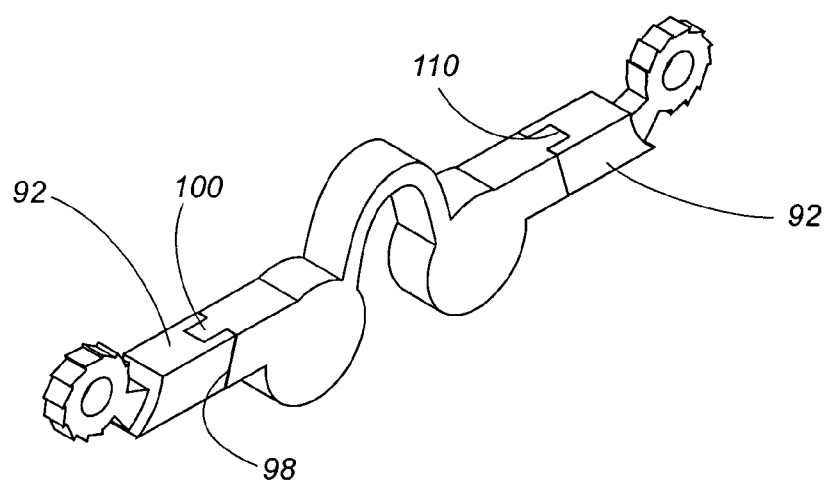
FIG. 29 is a perspective view of the joined connector links of FIG. 26.
Figure 26:
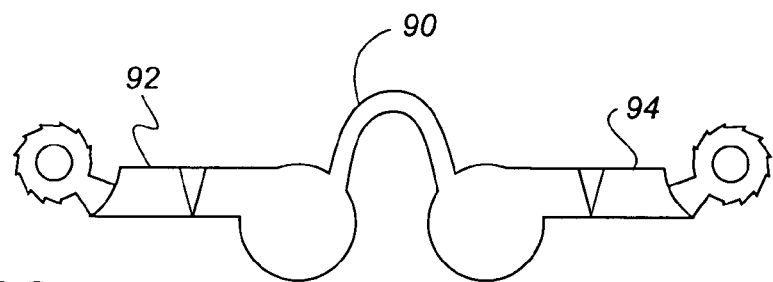
FIG. 26 is a side view showing the connector links of FIG. 22 joined together.
Figure 27:
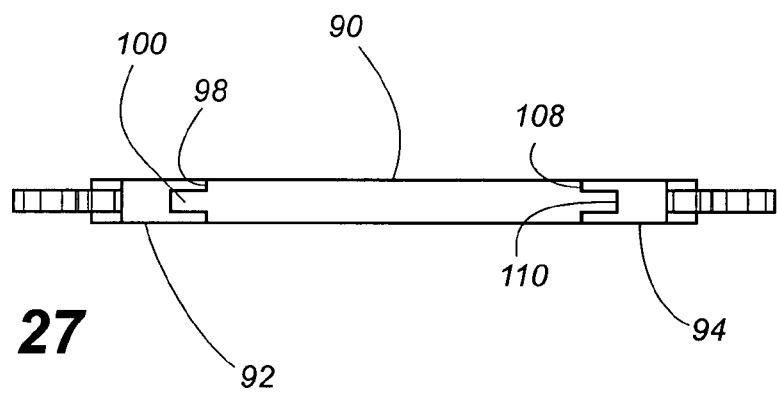
FIG. 27 is a top view of the joined connector links of FIG. 26.
Figure 28:
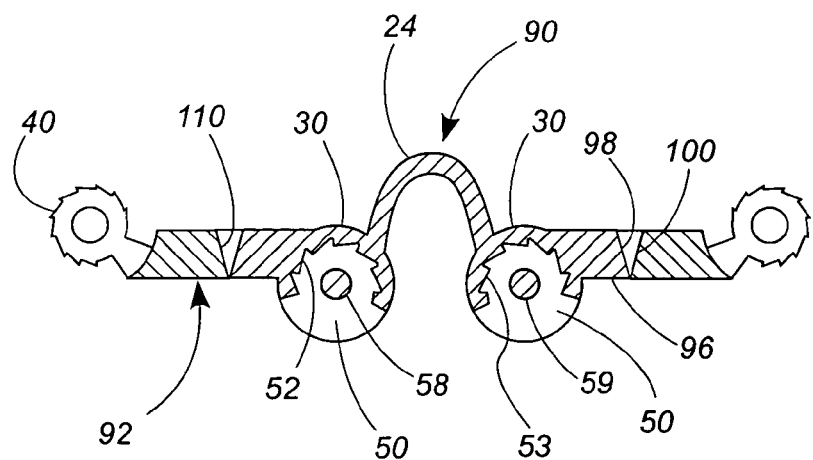
FIG. 28 is a cutaway view of FIG. 27.

Referring now to FIGS. 19–21, the termination links 80, 82 are the equivalent of link segments 22, 23 but without a connector 24. Determination links 80, 82 include disk-shaped head portions 28 and radial support members 30. A toothed wheel 40 is located at an end of the termination link 80, and a toothed wheel 41 is located at an end of the termination link 82. The termination link 80 includes a cavity 50 having an upper wall 52 with tooth-shaped recesses, and the termination link 82 includes a cavity 50 having an upper wall 53 with tooth-shaped recesses. A cylindrical spindle 58, 59 are formed in the center of each disk-shaped head portion 30 of the termination links 80, 82.

FIGS. 22–29 depict coupler links 90, 92, and 94. Referring first to FIGS. 22–25, a central coupler link 90 includes two disk-shaped head portions 30 linked by a connector 24. A radial support stub 96 extends substantially tangentially from each head portion 30. The end face 98 of each radial support stub 96 is beveled downward and outward. A tongue 100 extends outward from the end face 98 of each radial support stub 96. The outer edge of each tongue 100 is beveled upward and outward. Each head portion 30 defines a cavity 50 bounded by upper walls 52, 53 having tooth-shaped recesses. Cylindrical spindles 58, 59 are formed in the central portion of each cavity.

Each of the outer coupler links 92, 94 includes a radial support segment 106. At one end of each radial support segment 106 is a toothed wheel 40, 41. The opposite end 108 of each radial support segment 106 is beveled upward and outward, forming a complementary surface to the end face 98 of the radial support stubs 96 of the central coupler link 90. A groove 110 is formed in the end 108 of each radial support segment 106. The groove 110 is angled downward and outward, creating a complementary fit for a tongue 100 of the central coupler link 90.

FIGS. 26–29 illustrate the coupler links 90, 92, and 94 joined together. The tongues 100 of the central coupler link engage the corresponding grooves 110 of the radial support segments 106, and the beveled end faces 98 of the central coupler link confront the cooperatively beveled ends 108 of the radial support segments. When assembled in the manner shown in FIGS. 26–29, the coupler links 90, 92, and 94 cooperate to form the equivalent of a link 20 of the type previously described.

Figure 30:
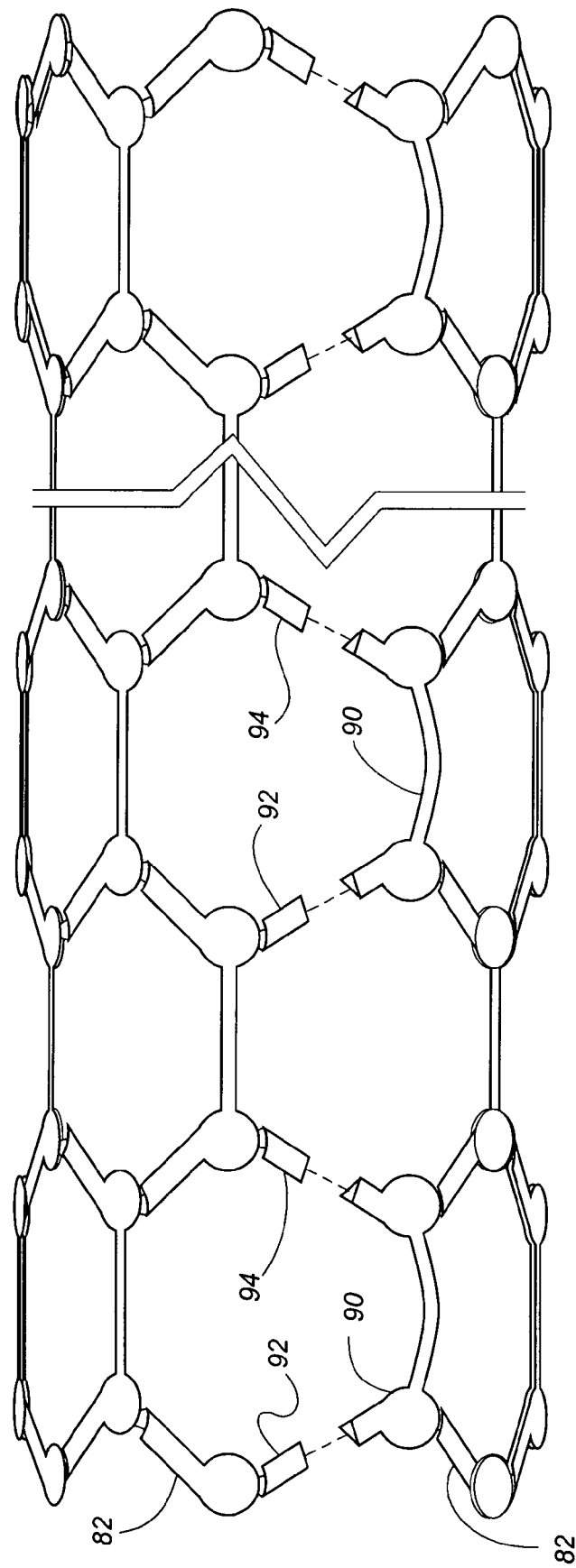
FIG. 30 is a side view of the panel of FIG. 18 rolled into a cylinder, with the connector links shown in unconnected, spaced-apart relation.
Figure 31:
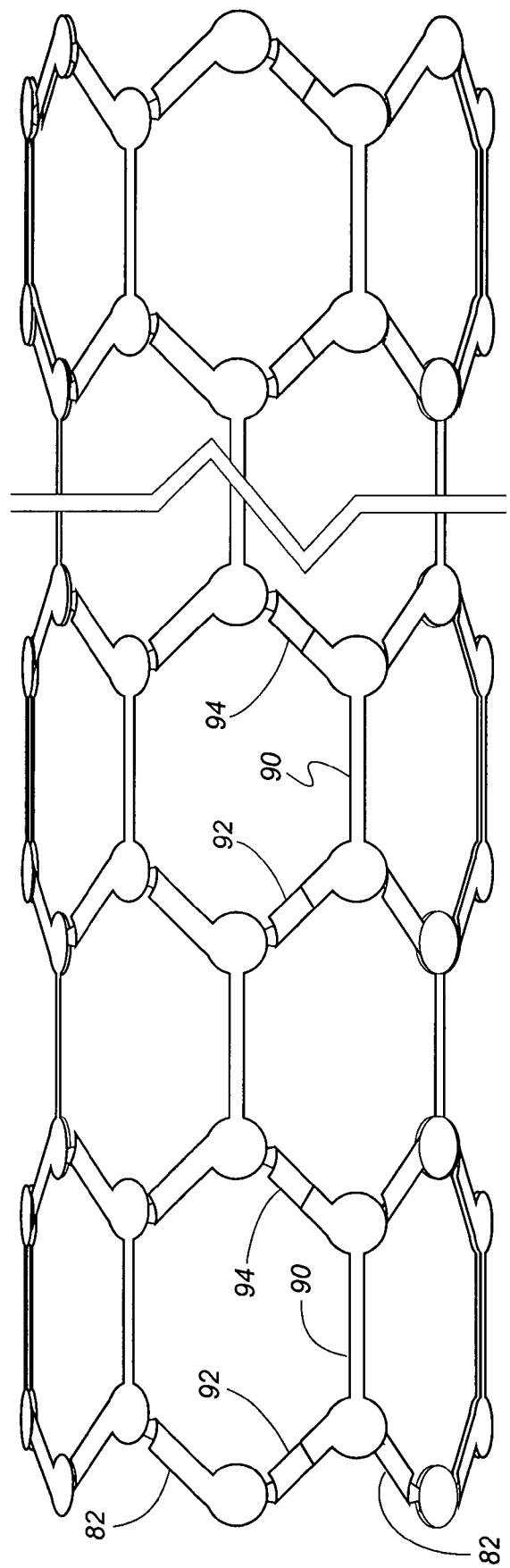
FIG. 31 is a side view of the panel of FIG. 18 with the connector links joined to form the panel into a cylinder.

FIGS. 30 and 31 show how the coupler links 90, 92, and 94 cooperate to fasten the upper and lower edges of the panel 75 when the panel is rolled into a cylindrical shape. With reference again to FIG. 18, central coupler links 90 are located at the upper edge of the panel 75, and outer coupler links 92, 94 are located at the lower edge of the panel. When the panel is rolled into a cylinder, as shown in FIGS. 30 and 31, the coupler links 92, 94 at the lower edge of the panel engage the central coupler links 90 at the upper edge of the panel to hold the panel in a tubular shape.

The stent can be constructed using any method available to those skilled in the art. However, specialized MEMS-based manufacturing methods are required in order to form the latching features on the scale of the disclosed embodiment. Some examples of the techniques that may be utilized are surface micro machining, photo lithography, electroplating, sacrificial molding, vacuum molding, and spin coating.

Preferably, the entire stent should be built at the initial stage in substantially its assembled form, as it would be impractical to assemble the interacting strut components at any later stage. In order to do this, the most traditional method would be to build up the stent on a planar surface. For a given thickness, the 2-D geometry is homogenous, lending itself well to the use of lithography mask patterns to deposit the stent material according to the desired pre-crimped geometry.

Fabrication of the stent 10 will now be explained with reference to FIGS. 32–48. In discussing FIGS. 32–48, the following numbering conventions will apply. Where there are numerous elements of the same type, for example, several links 20, the various links will be differentiated by a letter following the reference numeral. Thus three links would be designated by the reference numerals 20A, 20B, and 20C. Further, since the stent 10 is built-up as five separate layers, the various layers will be differentiated by a roman numeral from I to V following the letter. Thus the reference numeral 20A-I indicates the first layer of a first link. A reference numeral followed directly by a roman numeral without a letter, e.g., 20-I, refers to any element 20 in layer I.

Referring first to FIGS. 32 and 33, the first layer I includes the first layer of the various links, e.g. 20A-I, 20B-I, including left link segments 22A-I, 22B-I and right link segments 23A-I, 23B-I connected by connectors 24A-I, 24B-I. This layer forms the bottom wall of the containment joint, and there is no ratcheting wheel yet at this depth. The first layer is approximately 30 microns thick.

FIGS. 34 and 35 illustrate the second layer II of the stent 10. The second layer includes radial support members, e.g., 30A-II, 30B-II, upper walls 52A-II, 53A-II, 52B-II, and 53B-II, and spindles 58A-II, 59A-II, 58B-II, and 59B-II. Thus the second layer forms the initial wall and post of the containment joint. In the disclosed embodiment, the second layer II is approximately 5 microns thick. It will be understood that the second layer II in reality is not formed as a freestanding layer as depicted in FIGS. 34 and 35 but instead is formed directly on top of the first layer I. Thus FIGS. 34 and 35 are shown only for convenience of description.

FIGS. 36 and 37 showed the second layer II built up onto the first layer I. For the locations where some separation distance is required for the movement of parts relative to one another, these gaps can be created simply in the X, Y plane, using the standard lithography mask. In order to create a separation between parts in the depth direction, or 'Z' direction, a sacrificial layer may be deposited in the desired separation thickness. After construction of the subsequent layers, this sacrificial layer can be dissolved away, using an appropriate solvent that selectively dissolves only the sacrificial layer. Thus at this stage, the sacrificial layer is deposited at the sites under where the ratcheting wheel will reside in the next layer. The thickness of this layer defines the separation distance between the underside of the male latching wheel and the top surface of the bottom containment wall. In FIGS. 36 and 37, the sacrificial material is indicated by the reference numeral 115

Figure 38:
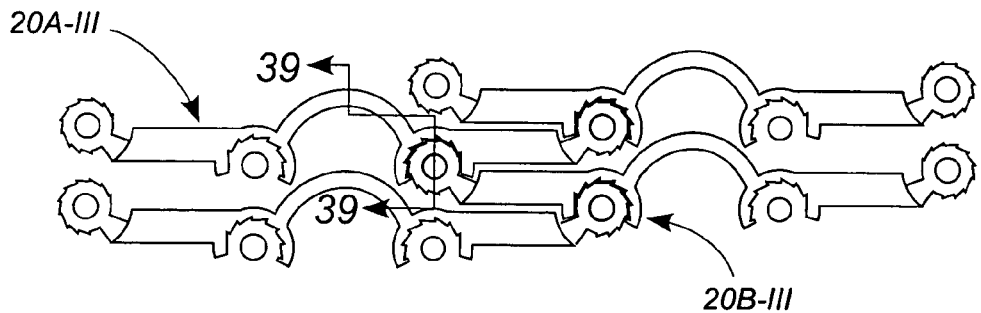
Figure 40:
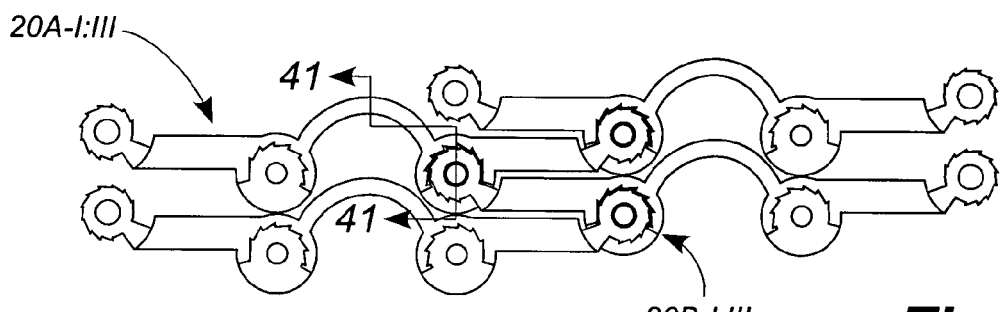
Figure 39:
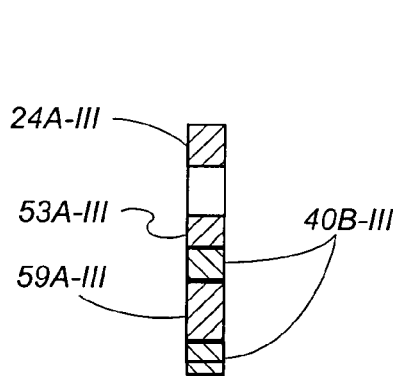
Figure 41:
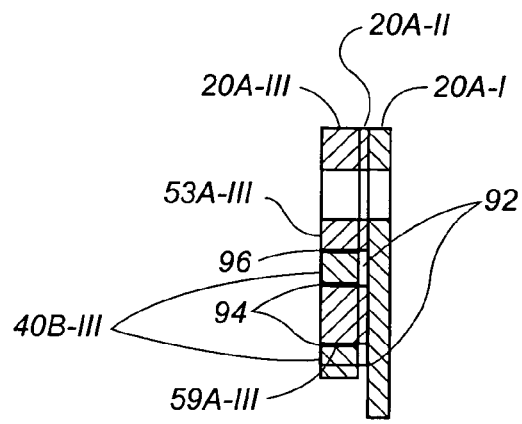
Figure 42:
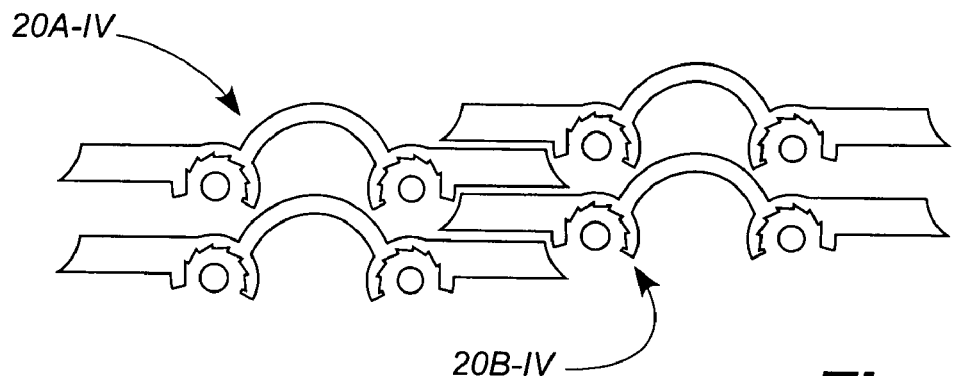
Figure 43:
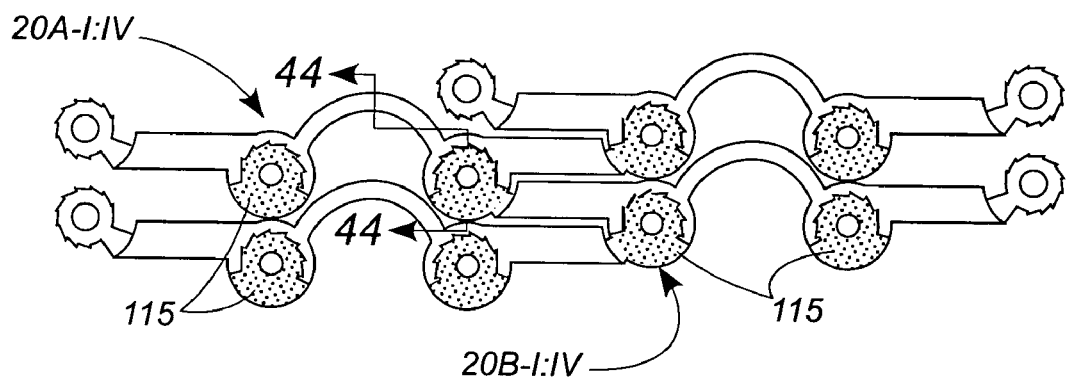
Figure 44:
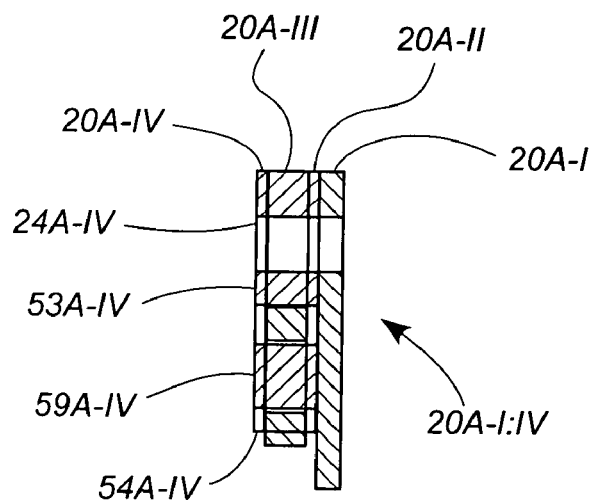
Figure 45:
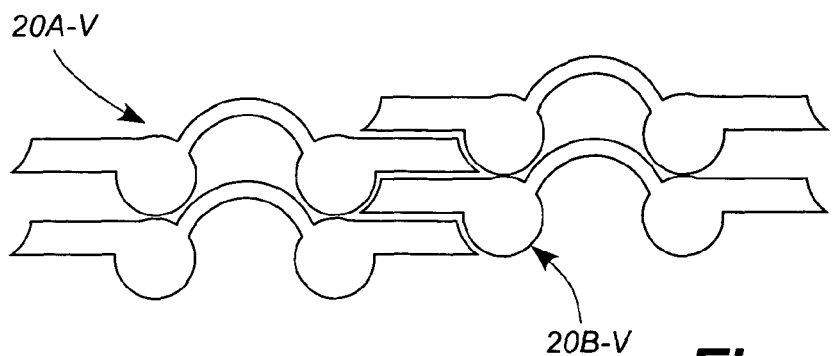
Figure 46:
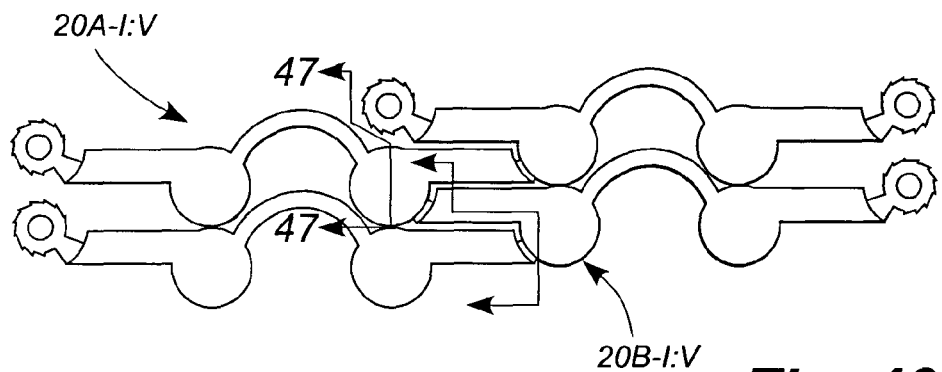
Figure 47:
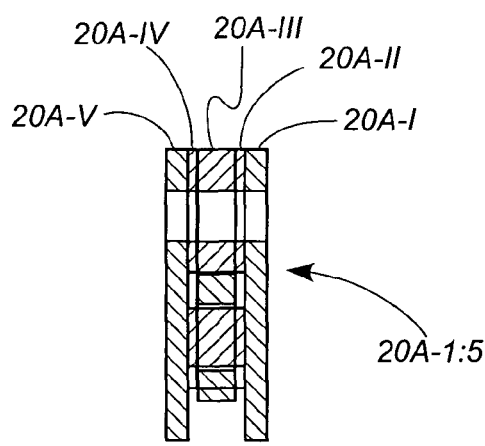
Figure 48:
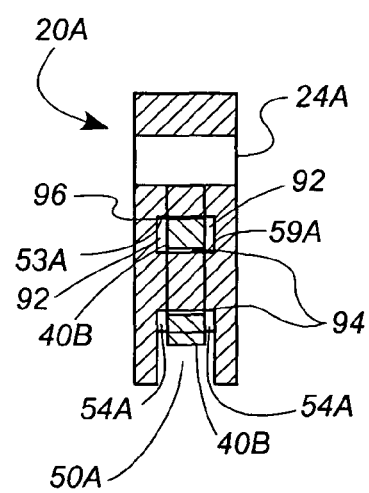

FIGS. 38 and 39 illustrate the third layer III. The third layer III is identical to the second layer II with the exception of the addition of the toothed wheels 40-III, 41-III and the corresponding neck portions 42-III joining the toothed wheels to the end of each radial support member 30-III. The toothed wheels 40, 41 are formed engaging the spindle 58, 59 of an adjacent link member 20. Also in this layer III, the walls and post of the containment joint continue to be built up. As can be seen in FIGS. 40 and 41, the walls 52, 53 are separated from the ratcheting wheel by a sufficient distance to allow the desired ratcheting characteristics.

With reference to FIGS. 42–48, the top two layers IV, V of the stent 10 are built the same as the second and first layers II, I. A sacrificial layer is used to create the separation gap over the ratcheting wheel, and finally the top wall of the containment joint is formed.

After building up the crimped stent on a planar surface, the next formation step is to roll the stent into a cylindrical shape and fuse the free ends together. To do this, the stent can be rolled around a pin that has an outer diameter that represents the desired pre-crimped inner diameter of the stent. A loading tube can be used to facilitate assembly. This loading tube has an inner diameter that represents the pre-crimped outer diameter of the stent and an axial slit at one end. The tube will be loaded over the stent with the slit aligned with the free ends. As the tube is advanced, the tab ends of the top and bottom struts can be assembled and aligned into one another and the tube can be advanced over the assembled strut. After all the coupler links 90, 91, 92 are assembled together and fully contained by the loading tube and the pin, they can be permanently fused using some form of localized heat bonding method, such as laser welding, known to those skilled in the art.

After bonding the free ends of the coupler links together, the pre-crimped stent should be heat treated, setting the material structure into the cylindrical form. During this step, care should be taken not to overheat the part so as to avoid fusing the joint components together. After completion, the loading tube and pin can be removed, resulting in a pre-crimped stent component.

Alternately, the building up of the stent 10 can be performed on a cylindrical substrate, rather than on a flat surface. This requires a specialized lithography setup that is capable of converting a planar lithography image onto a cylindrical surface. This can be done by indexing the rotation of a continuous lithography mask with the rotation of a cylindrical substrate. Although more complex, the advantage of this manufacturing method is that no final forming processes are necessary to form the stent into a cylindrical shape, and no coupler links 90, 91, 92 need be formed.

The use of pivotable links instead of conventional joints means that no plastic deformation is required at the joints in order to retain the expanded state. Instead, micro latching elements are integrated into the intersections between the radial support elements. These latching features allow angular expansion between the radial support elements in the rotational direction that results in radial expansion of the structure. At the same time, the latches restrict movement in the opposite direction that results in reduction in diameter from the expanded state. Thus the stent, once expanded, will not contract again due to radially inward forces exerted by the wall of the vessel.

In addition, because mechanical movement of the joint, rather than plastic deformation, is employed to expand the stent, alternate materials such as biodegradable polymers can be used in a balloon-expandable stent. This design allows expansion by a balloon in the same manner that has been previously described for traditional balloon-expandable stents.

The stent can be made from any material that is suitable for use as a medical implant. In the disclosed embodiment, however, the stent will serve only a temporary function as a medicated splint. The desired function of the stent will be to promote and guide the healing process after dilation. After the healing has completed, its function has passed and it will dissolve away into the tissue.

This described effect can be achieved by constructing the stent using a biodegradable polymer, such as poly (L-lactide) (L-PLA) or poly(glycolide) (PGA), that is embedded or coated with a pharmacological agent that prevents restenosis. Constructed in this manner, the stent will provide scaffolding to the vessel treatment site long enough to guide the healing response around its structural elements. During this time, the stent will elute pharmacological agents that will prevent overgrowth of the healing response, or "restenosis" of the vessel. After the approximate time that the healing process has completed, the stent will cease to function as a structural component, gradually degrading into the tissue.

The ratcheting properties of the joints, such as the forces required to expand and close the joints, can be optimized through the adjustment of the design parameters. As will be readily apparent to those skilled in the art, there are a number of parameters which affect the ratcheting properties, and an optimized variation of these parameters should yield the desired ratcheting properties. Some examples of these design parameters are the distance between teeth, quantity of teeth per joint, and the height, shape, and slopes of the teeth. Material properties and wall thickness of the containment joint are also parameters that will have impact to the ratcheting properties. Another key design parameter is the separation distance between the ratchet wheel and the inner surfaces of the containment joint.

If additional improvement of the ratcheting properties is needed, voids can also be incorporated under the teeth of the ratchet wheel and/or the receiving surface. The inclusion of these voids further facilitates deflection of the surfaces during opening.

Referring now to FIGS. 53–56, to facilitate crimping of the stent onto the balloon, an alternate version of a stent includes modifications to allow a slight reduction in diameter during initial crimping. In the original design, the stent 10 can only be expanded, and not reduced in diameter, so it would need to be loaded onto the balloon at its final crimped diameter. In the alternate embodiment of the stent, the inner diameter of the stent can be slightly enlarged to facilitate slipping the stent over the balloon. Then, once in position, the stent can be forced down onto the balloon by a crimping tool that would perform in an equivalent manner as those that are typically used for crimping metallic stents.

To achieve this behavior, the stent of the alternate embodiment is provided with links 220 that only partially restrict movement in either direction in the lower expansion range, but restrict reverse movement more substantially at the upper end of the expansion range. Also, the starting position of the neck in the side opening of the containment joint should be such that some initial rotation is allowed in the downward crimping direction.

Figure 53:
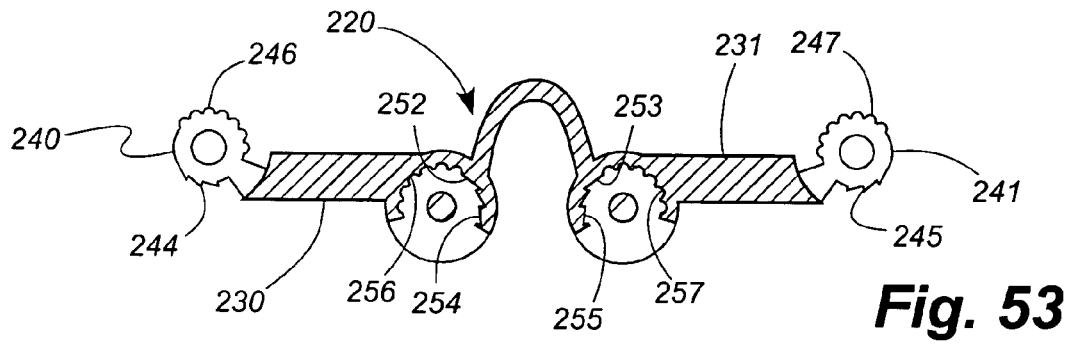
FIG. 53 is a side view of the link of the alternate embodiment.

FIG. 53 shows a link 220 which forms a part of the stent of the alternate embodiment. The link 220 is in most respects similar to the link 20 previously described, and only the differences will be discussed.

The link 220 includes wheels 240, 241 which have a smaller number of gear teeth 244, 245 formed on their lower peripheries. Along their upper peripheries, the wheels 240, 241 include a plurality of rounded bumps 246, 247. Likewise, the walls 252, 253 have a portion closest to the center of the link 220 which has tooth-shaped indentations 254, 255 cooperatively configured to receive the gear teeth 244, 245. The portions of the walls 252, 253 furthest from the center of the link 220 include a plurality of rounded recesses 256, 257 configured to cooperatively receive the rounded bumps 246, 247 on the wheel.

Figure 54:
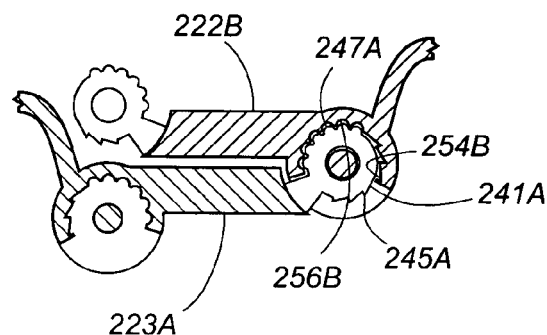

FIG. 54 shows a first link segment 223A of a first link engaging a cooperating link segment 222B of a second link. When the link segments 223A., 222B are in their closed configuration, as illustrated in FIG. 54, the rounded bumps 247A of the wheel 241A engage the cooperating rounded recesses 256B of the other link segment.

Figure 55:
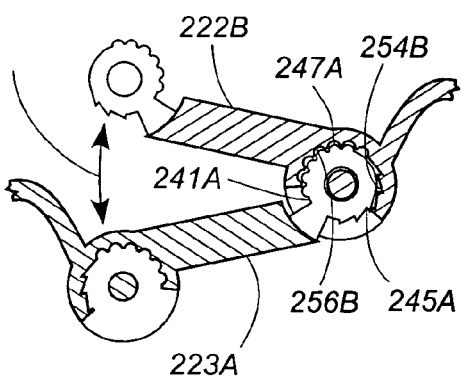
FIG. 55 is a side view showing the two link segments of FIG. 54 only partially opened so that they can be closed again.
Figure 56:
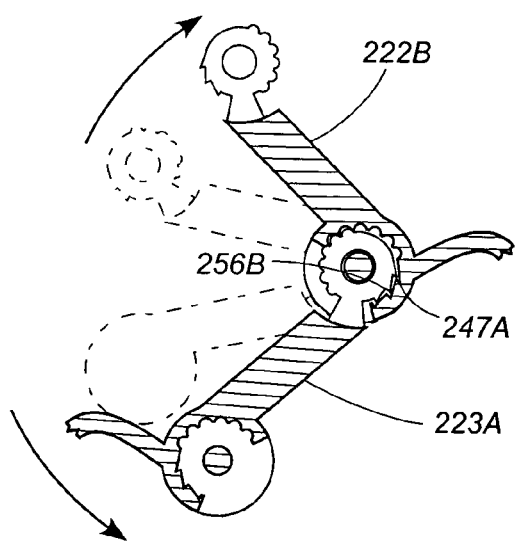
FIG. 56 is a side view showing the two link segments of FIG. 54 opened to the point that they cannot be re-closed but can only be further opened.

Because the rounded bumps 247A permit rotation of the wheel 241A in both directions, the link segments 223A, 222B are able to rotate both open and closed within certain limits, as shown in FIG. 55. However, once the link segments 223A, 222B rotate to an extent that the gear teeth 245A on the wheel 241A engage the cooperating tooth-shaped recesses 254B in the other link segment, as shown in FIG. 56, the links can henceforth rotate only to open or expand the stent.

The advantage of this arrangement is that a stent comprised of links 220 can be slightly opened or expanded to permit the stent to slide easily over the forward end of a balloon catheter. Once positioned over the balloon, the stent can be crimped or closed to secure it snugly to the balloon. When the balloon is later inflated, the stent will re-open and, once the gear teeth in the wheel 241A engage the cooperating tooth-shaped recesses in the opposite link segment, the stent will maintain its opened condition against radially inward forces.

Figure 57:
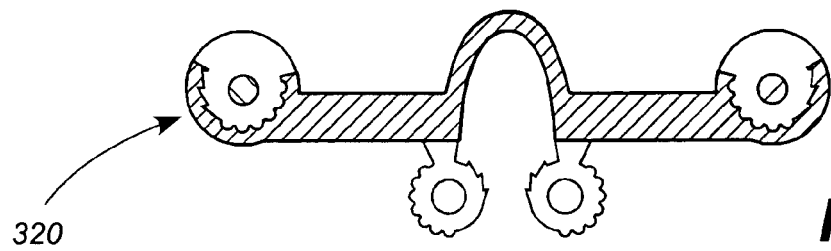
FIG. 57 is another embodiment of a link.

FIG. 57 shows an alternate embodiment of a link 320. The link 320 is characterized by the male and female ratchet members being switched in location, that is, the toothed wheels are on the lower inside of the link, and the walls with tooth-shaped recesses are on the upper outside edges of the link.

Figure 58:
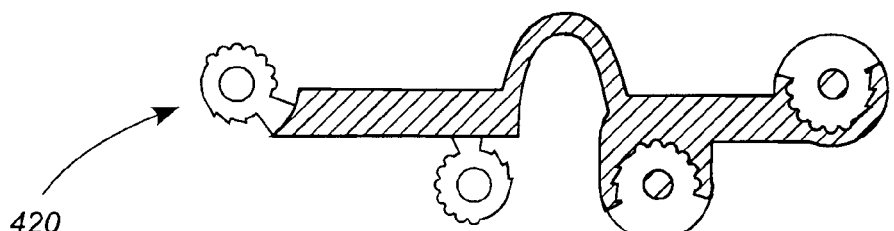
FIG. 58 is still another embodiment of a link.

FIG. 58 shows a link 420 in which both male ratchet members are on one side of the link, and both female ratchet members are on the opposite side of the link.

Figure 59:
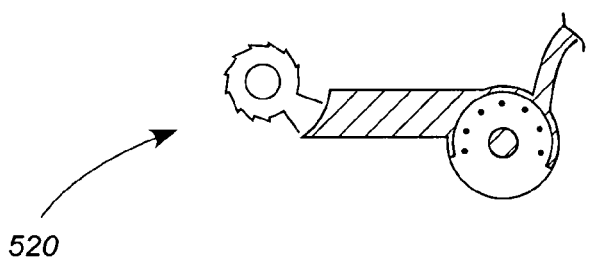
FIG. 59 is yet another embodiment of a link.

FIG. 59 depicts a link 520 in which the walls with tooth-shaped recesses are replaced by discrete pins projecting perpendicular to the plane of the page.

Figure 60:
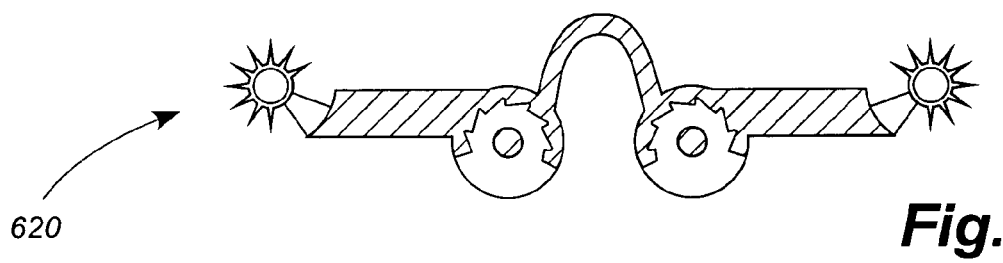
FIG. 60 is a further embodiment of a link.

FIG. 60 illustrates a link 620 in which the toothed wheel is replaced with a plurality of radial fingers.

FIG. 61 shows a link 720 in which the toothed wheel has no bore, and the containment joint has no post. Instead, the wheels are maintained in engagement with the walls by means of the walls proscribing a radius of greater than 180°.

As will be appreciated, the disclosed stent overcomes the disadvantages shown in the prior art. First, the disclosed stent provides a virtually continuous increment of expansion. The increment of the latching mechanism is on the micron scale and is distributed over all joints around the stent. Thus the stent diameter increment between locking states is negligible.

In addition, the disclosed stent minimizes performance degradation. Because the latching elements themselves are incorporated into the structural element joints, they do not add bulk to the stent. For this reason, system performance comparable or superior to non-latching stents should be achievable with a stent design that incorporates the micro-latching features.

Further, the unit structure of the disclosed stent is inherently stronger than standard balloon-expandable or self-expanding stents because of the use of latching elements. Applied in the appropriate manner, stent-latching mechanisms can also improve the inherent strength of the individual structural elements. This improved strength enables the designer to reduce the stent material stiffness without sacrificing radial strength. This capability also allows the designer to maintain an equivalent dimensional scale as is currently the standard for non-latching balloon-expandable stents, but use softer materials, such as biodegradable polymers in place of metals.

Finally, it will be understood that the preferred embodiment has been disclosed by way of example, and that other modifications may occur to those skilled in the art without departing from the scope and spirit of the appended claims.

What is claimed is:

1. A link for use in constructing an intravascular stent, comprising a flexible connector having first and second ends; a first radial support member having a first end attached to said first end of said connector and having a second end extending away from said connector; a second radial support member having a first end attached to said second end of said connector and having a second end extending away from said connector; a first rotary ratchet means disposed at said first end of said first radial support member; a second rotary ratchet means disposed at said first end of said second radial support member; a third rotary ratchet means complementary to said second rotary ratchet means and disposed at said second end of said first radial support member; and, a fourth rotary ratchet means complementary to said first rotary ratchet means and disposed at said second end of said second radial support member.

2. The link of claim 1, wherein one of said second and third rotary ratchet means and one of said first and fourth rotary ratchet means comprises a wheel with angled teeth formed on its periphery.

3. A link for use in constructing a medical device comprising a flexible connector having first and second ends; a first radial support member having a first end attached to said first end of said connector and having a second end extending away from said connector; a second radial support member having a first end attached to said second end of said connector and having a second end extending away from said connector; a first rotary ratchet means disposed at said first end of said first radial support member; a second rotary ratchet means disposed at said first end of said second radial support member; a third rotary ratchet means complementary to said second rotary ratchet means and disposed at said second end of said first radial support member; and a fourth rotary ratchet means complementary to said first rotary ratchet means and disposed at said second end of said second radial support member; one of said second and third rotary ratchet means and one of said first and fourth rotary ratchet means comprises a wheel with angled teeth formed on its periphery; one of said second and third rotary ratchet means and one of said first and fourth rotary ratchet means comprises a wheel with angled teeth formed on its periphery; the other of said second and third rotary ratchet means and the other of said first and fourth rotary ratchet means comprises walls defining a circular recess complementary to said wheel, said walls having cutouts complementary to said angled teeth formed therein.

4. The link of claim 3, further comprising an upstanding post formed at the center of each of said circular recesses; and wherein each of said wheels defines a hole therethrough having dimensions complementary to said post.

5. A medical device comprised of a plurality of interconnected links, a plurality of said links comprising a flexible connector having first and second ends; a first radial support member having a first end attached to said first end of said connector and having a second end extending away from said connector; a second radial support member having a first end attached to said second end of said connector and having a second end extending away from said connector; a first rotary ratchet means disposed at said first end of said first radial support member; a second rotary ratchet means disposed at said first end of said second radial support member; a third rotary ratchet means complementary to said second rotary ratchet means and disposed at said second end of said first radial support member; and a fourth rotary ratchet means complementary to said first rotary ratchet means and disposed at said second end of said second radial support member; each one of said plurality of links being surrounded by and connected to four identical adjacent links, wherein a first identical adjacent link has its fourth rotary ratchet means engaged with the first rotary ratchet means of the one link; wherein a second identical adjacent link has its third rotary ratchet means engaged with the second rotary ratchet means of the one link; wherein a third identical adjacent link has its second rotary ratchet means engaged with the third rotary ratchet means of the one link; and wherein a fourth identical adjacent link has its first rotary ratchet means engaged with the fourth rotary ratchet means of the one link.

6. The medical device of claim 5, wherein said ratchet means are configured such that said first radial support members are permitted by said rotary ratchet means to rotate only clockwise and said second radial support members are permitted by said rotary ratchet means to rotate only counterclockwise.

7. The medical device of claim 6, wherein said plurality of links is formed into a cylinder, said cylinder being expandable but, once expanded, not contractible.

8. A medical device that includes a body section, said body section includes a plurality of links, at least one of said links enabling at least a portion of said body section to expand and to restist contracting once said body section is at least partially expanded, at least one of said links including at least one link segment, said link segment including a head portion and a support member, said support member having first and second ends, first end of said support member rotatably connected to said head portion, said first end of said support member and said head portion including an engagement arrangement that has at least one engagement surface designed to limit a direction of rotation of said support member in a single direction relative to said head portion.

9. The medical device as defined in claim 8, wherein said engagement arrangement includes a plurality of engagement surfaces designed to limit a direction of rotation of said support member in a single direction relative to said head portion.

10. The medical device as defined in claim 9, wherein all said engagement surfaces are designed to limit a direction of rotation of said support member in a single direction relative to said head portion.

11. The medical device as defined in claim 8, wherein said engagement arrangement includes at least one engagement surface designed to allow rotation of said support member in a plurality of directions and at least one engagement surface designed to limit a direction of rotation of said support member in a single direction relative to said head portion.

12. The medical device as defined in claim 9, wherein said engagement arrangement includes a plurality engagement surfaces designed to allow rotation of said support member in a plurality of directions and a plurality engagement surfaces designed to limit a direction of rotation of said support member in a single direction relative to said head portion.

13. The medical device as defined in claim 8, wherein a plurality of said links enable at least a portion of said body section to expand and to restrict contracting once said body section is at least partially expanded, a plurality of said links including at least one link segment.

14. The medical device as defined in claim 10, wherein a plurality of said links enable at least a portion of said body section to expand and to restrict contracting once said body section is at least partially expanded, a plurality of said links including at least one link segment.

15. The medical device as defined in claim 12, wherein a plurality of said links enable at least a portion of said body section to expand and to restrict contracting once said body section is at least partially expanded, a plurality of said links including at least one link segment.

16. The medical device as defined in claim 10, wherein said engagement arrangement includes a ratcheting arrangement, said ratcheting arrangement including a plurality of engagement surfaces at least partially formed from a plurality of teeth and/or bumps and a plurality of recesses.

17. The medical device as defined in claim 14, wherein said engagement arrangement includes a ratcheting arrangement, said ratcheting arrangement including a plurality of engagement surfaces at least partially formed from a plurality of teeth and/or bumps and a plurality of recesses.

18. The medical device as defined in claim 12, wherein said engagement arrangement includes a ratcheting arrangement, said ratcheting arrangement including a plurality of engagement surfaces at least partially formed from a plurality of teeth and/or bumps and a plurality of recesses.

19. The medical device as defined in claim 15, wherein said engagement arrangement includes a ratcheting arrangement, said ratcheting arrangement including a plurality of engagement surfaces at least partially formed from a plurality of teeth and/or bumps and a plurality of recesses.

20. The medical device as defined in claim 8, wherein at least two of said links are connected together by a flexible connector.

21. The medical device as defined in claim 10, wherein at least two of said links are connected together by a flexible connector.

22. The medical device as defined in claim 12, wherein at least two of said links are connected together by a flexible connector.

23. The medical device as defined in claim 16, wherein at least two of said links are connected together by a flexible connector.

24. The medical device as defined in claim 17, wherein at least two of said links are connected together by a flexible connector.

25. The medical device as defined in claim 18, wherein at least two of said links are connected together by a flexible connector.

26. The medical device as defined in claim 19, wherein at least two of said links are connected together by a flexible connector.

27. The medical device as defined in claim 20, wherein said connector enables said links to change in distance from one another when said body section is expanded.

28. The medical device as defined in claim 24, wherein said connector enables said links to change in distance from one another when said body section is expanded.

29. The medical device as defined in claim 26, wherein said connector enables said links to change in distance from one another when said body section is expanded.

30. The medical device as defined in claim 8, wherein at least one support member has a second end that includes at least a portion of an engagement arrangement.

31. The medical device as defined in claim 28, wherein at least one support member has a second end that includes at least a portion of an engagement arrangement.

32. The medical device as defined in claim 29, wherein at least one support member has a second end that includes at least a portion of an engagement arrangement.

33. The medical device as defined in claim 30, wherein at least one support member has a second end including an engagement arrangement designed to limit a direction of rotation of said support member in a single direction relative to another head portion.

34. The medical device as defined in claim 31, wherein at least one support member has a second end including an engagement arrangement designed to limit a direction of rotation of said support member in a single direction relative to another head portion.

35. The medical device as defined in claim 32, wherein at least one support member has a second end including an engagement arrangement designed to limit a direction of rotation of said support member in a single direction relative to another head portion.

36. The medical device as defined in claim 33, wherein said engagement arrangement on said second end includes a ratcheting arrangement, said ratcheting arrangement including a plurality of engagement surfaces at least partially formed from a plurality of teeth and/or bumps and a plurality of recesses.

37. The medical device as defined in claim 34, wherein said engagement arrangement on said second end includes a ratcheting arrangement, said ratcheting arrangement including a plurality of engagement surfaces at least partially formed from a plurality of teeth and/or bumps and a plurality of recesses.

38. The medical device as defined in claim 35, wherein said engagement arrangement on said second end includes a ratcheting arrangement, said ratcheting arrangement including a plurality of engagement surfaces at least partially formed from a plurality of teeth and/or bumps and a plurality of recesses.

39. The medical device as defined in claim 36, wherein said ratcheting arrangement includes a wheel with angled teeth formed on its periphery and a plurality of teeth recess, said wheel at least partially formed in said head portion and said teeth recesses at least partially formed on said first end of said support member.

40. The medical device as defined in claim 8, wherein said body portion at least partially forms a stent.

41. The medical device as defined in claim 37, wherein said body portion at least partially forms a stent.

42. The medical device as defined in claim 38, wherein said body portion at least partially forms a stent.

43. The medical device as defined in claim 8, wherein said body portion is at least partially formed from a bio-degradable material.

44. The medical device as defined in claim 41, wherein said body portion is at least partially formed from a bio-degradable material.

45. The medical device as defined in claim 42, wherein said body portion is at least partially formed from a bio-degradable material.

46. The medical device as defined in claim 8, wherein said body portion includes a pharmacological agent, is coated with a pharmacological agent, or combinations thereof.

47. The medical device as defined in claim 44, wherein said body portion includes a pharmacological agent, is coated with a pharmacological agent, or combinations thereof.

48. The medical device as defined in claim 45, wherein said body portion includes a pharmacological agent, is coated with a pharmacological agent, or combinations thereof.

* * * * *